(12) United States Patent
Satoh et al.

(10) Patent No.: US 11,607,201 B2
(45) Date of Patent: Mar. 21, 2023

(54) ULTRASOUND DIAGNOSTIC APPARATUS AND OPERATION METHOD OF ULTRASOUND DIAGNOSTIC APPARATUS BY DETERMINING DEPOLARIZATION TO NECESSITATE SUPPLY OF POLARIZATION VOLTAGE TO ULTRASOUND TRANSDUCERS

(71) Applicant: FUJIFILM Corporation, Tokyo (JP)

(72) Inventors: Yoshiaki Satoh, Ashigarakami-gun (JP); Katsuya Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 766 days.

(21) Appl. No.: 16/419,595

(22) Filed: May 22, 2019

(65) Prior Publication Data

US 2020/0000439 A1 Jan. 2, 2020

(30) Foreign Application Priority Data

Jun. 29, 2018 (JP) .............................. JP2018-124632

(51) Int. Cl.
*A61B 8/00* (2006.01)
*A61B 8/08* (2006.01)
(Continued)

(52) U.S. Cl.
CPC .................. *A61B 8/56* (2013.01); *A61B 8/12* (2013.01); *A61B 8/467* (2013.01); *A61B 8/5207* (2013.01);
(Continued)

(58) Field of Classification Search
CPC .. A61B 8/56; A61B 8/12; A61B 8/467; A61B 8/5207; A61B 8/58; B06B 1/06
See application file for complete search history.

(56) References Cited

U.S. PATENT DOCUMENTS

2004/0260181 A1 12/2004 Makita et al.
2007/0167814 A1* 7/2007 Wakabayashi ........... A61B 8/12
600/459
(Continued)

FOREIGN PATENT DOCUMENTS

CN 102670259 A 9/2012
JP 9-141859 A 8/1997
(Continued)

OTHER PUBLICATIONS

Extended European Search Report for corresponding European Application No. 19174171.9, dated Nov. 20, 2019.
(Continued)

*Primary Examiner* — Serkan Akar
*Assistant Examiner* — Amal Aly Farag
(74) *Attorney, Agent, or Firm* — Birch, Stewart, Kolasch & Birch, LLP

(57) ABSTRACT

An ultrasound transducer unit including a plurality of ultrasound transducers transmits and receives ultrasound waves to and from an inside of a subject. In a case where a checking operation unit is operated, a controller controls a driving voltage supply unit such that a driving voltage is supplied with all of the plurality of ultrasound transducers as driving target transducers. In a case where the checking operation unit is operated, a depolarization determination unit calculates, for each ultrasound transducer, a reception sensitivity in a case where an ultrasound wave is received by driving all of the plurality of ultrasound transducers as the driving target transducers, and determines whether or not a depolarization determination value calculated from the reception sensitivity of each ultrasound transducer satisfies numerical conditions. If the numerical conditions are satisfied, a polarization voltage supply unit supplies a polarization voltage to each of the plurality of ultrasound transducers.

19 Claims, 12 Drawing Sheets

(51) Int. Cl.
  *A61B 8/12* (2006.01)
  *B06B 1/06* (2006.01)
  *B06B 1/02* (2006.01)

(52) U.S. Cl.
  CPC .............. *A61B 8/58* (2013.01); *B06B 1/0207* (2013.01); *B06B 1/06* (2013.01); *B06B 1/0625* (2013.01); *B06B 2201/20* (2013.01); *B06B 2201/40* (2013.01)

(56) References Cited

U.S. PATENT DOCUMENTS

| | | | |
|---|---|---|---|
| 2008/0111452 | A1 | 5/2008 | Koizumi et al. |
| 2011/0112405 | A1* | 5/2011 | Barthe ................. A61B 8/0858 600/459 |
| 2012/0319529 | A1 | 12/2012 | Nakazawa et al. |
| 2012/0323514 | A1 | 12/2012 | Nakazawa et al. |
| 2017/0067858 | A1* | 3/2017 | Segall ...................... A61B 8/58 |

FOREIGN PATENT DOCUMENTS

| | | |
|---|---|---|
| JP | 2004-296784 A | 10/2004 |
| JP | 2008-120665 A | 5/2008 |
| JP | 2011-5024 A | 1/2011 |
| JP | 2012-139460 A | 7/2012 |
| JP | 2013-5137 A | 1/2013 |
| JP | 2013-161955 A | 8/2013 |
| JP | 2015-62621 A | 4/2015 |

OTHER PUBLICATIONS

Japanese Notice of Reasons for Refusal for corresponding Japanese Application No. 2021-150883, dated Oct. 11, 2022, with an English translation.
Extended European Search Report for corresponding European Application No. 22173498.1, dated Nov. 24, 2022.
Japanese Office Action for corresponding Japanese Application No. 2021-150883, dated Jan. 4, 2023, with English translation.

* cited by examiner

ULTRASOUND DIAGNOSTIC APPARATUS AND OPERATION METHOD OF ULTRASOUND DIAGNOSTIC APPARATUS BY DETERMINING DEPOLARIZATION TO NECESSITATE SUPPLY OF POLARIZATION VOLTAGE TO ULTRASOUND TRANSDUCERS

CROSS-REFERENCE TO RELATED APPLICATIONS

The present application claims priority under 35 U.S.C. § 119 to Japanese Patent Application No. 2018-124632, filed on Jun. 29, 2018. Each of the above application(s) is hereby expressly incorporated by reference, in its entirety, into the present application.

BACKGROUND OF THE INVENTION

1. Field of the Invention

The present invention relates to an ultrasound diagnostic apparatus and an operation method of an ultrasound diagnostic apparatus and in particular, to an ultrasound diagnostic apparatus including a plurality of ultrasound transducers, which are disposed inside a subject and driven to transmit and receive ultrasound waves, and an operation method of the ultrasound diagnostic apparatus.

2. Description of the Related Art

An ultrasound diagnostic apparatus that acquires an ultrasound image of the inside of a subject by transmitting and receiving ultrasound waves by driving a plurality of ultrasound transducers inside the subject (for example, inside the body of a patient) is already known. In the ultrasound diagnostic apparatus described above, the plurality of ultrasound transducers are, for example, single crystal transducers that are piezoelectric elements, and are usually used in a polarized state. The ultrasound transducer that is a single crystal transducer can receive ultrasound waves with high sensitivity, but a depolarization phenomenon in which the degree of polarization decreases as the driving time increases may occur. In a case where a depolarization phenomenon occurs, the reception sensitivity of the ultrasound transducer decreases, which may affect the image quality of the ultrasound image.

In particular, in the case of transmitting and receiving ultrasound waves by driving each ultrasound transducer inside the subject, since it is necessary to set the frequency of the ultrasound wave to a high frequency band of 7 MHz to 8 MHz level, a transducer having a relatively small thickness is used. However, as the thickness of the transducer decreases, the risk of occurrence of a depolarization phenomenon increases.

For this reason, techniques for countermeasures against depolarization in the ultrasound diagnostic apparatus have been developed so far. For example, an ultrasound diagnostic apparatus (referred to as a "piezoelectric sensor apparatus" in JP2013-005137A) described in JP2013-005137A has a piezoelectric element having a piezoelectric body and a pair of electrodes interposing the piezoelectric body therebetween, a detection circuit for performing detection processing for detecting a detection signal output from the piezoelectric element, and a polarization processing circuit for performing polarization processing by applying a polarization voltage to the piezoelectric element. In the ultrasound diagnostic apparatus described in JP2013-005137A having such a configuration, polarization processing is performed at a timing at which the electric power is supplied, a timing at which a request signal for executing detection processing is input (each reception timing), or a timing at which a predetermined standby transition time has passed after the end of detection processing, for example. Therefore, even in a case where a depolarization phenomenon occurs in the piezoelectric element, the piezoelectric element can be polarized again. As a result, it is possible to maintain the reception sensitivity of the piezoelectric element.

As another example, an ultrasound diagnostic apparatus (referred to as a "piezoelectric sensor apparatus" in JP2013-161955A) described in JP2013-161955A has a piezoelectric element, a polarization checking element for checking the polarization state of the piezoelectric element, a polarization processing unit for performing polarization processing by applying a polarization voltage to the piezoelectric element, and a controller for controlling the polarization timing of the polarization processing unit. In a case where the apparatus power is turned on, the controller acquires a characteristic value corresponding to the amount of polarization of the polarization checking element, determines whether or not the polarization characteristic of the piezoelectric element is unstable based on the characteristic value, and causes the polarization processing unit to perform polarization processing in a case where it is determined that the piezoelectric element is unstable. Therefore, even in a case where the polarization characteristic of the piezoelectric element becomes unstable, the piezoelectric element is subjected to polarization processing. As a result, since it is possible to return the polarization characteristic of the piezoelectric element to a state before degradation, it is possible to prevent the performance of the ultrasound diagnostic apparatus from lowering.

In the ultrasound diagnostic apparatus described in each of JP2013-005137A and JP2013-161955A, however, the timing at which the state (depolarization) of the piezoelectric element is determined or the timing of repolarization occurs is set to a predetermined timing, such as a timing at which the electric power is supplied. Therefore, in the ultrasound diagnostic apparatus described in each of JP2013-005137A and JP2013-161955A, it is necessary to wait for the above-described timing in order to restore the polarization of the piezoelectric element, and this may cause the time required for the entire ultrasound diagnosis to be excessively long.

In the ultrasound diagnostic apparatus described in JP2013-161955A, in order to check the polarization state of the piezoelectric element, the polarization checking element is separately provided. In such a case, since the piezoelectric checking element is provided, the size of the ultrasound probe to be inserted into the patient's body in the apparatus is increased. This may have an adverse effect on the operability (more specifically, easiness of insertion into the body).

On the other hand, unlike the ultrasound diagnostic apparatuses described in JP2013-005137A and JP2013-161955A, a technique capable of determining the state of the piezoelectric element at a desired timing has already been developed (for example, refer to JP2012-139460A).

The ultrasound diagnostic apparatus described in JP2012-139460A has an ultrasound probe including a piezoelectric element, a storage unit for storing a threshold value of a physical quantity (specifically, a voltage value of a reception signal) that changes with the degree of depolarization of the piezoelectric element, and a detection unit for detecting the physical quantity in the ultrasound probe. In the ultrasound diagnostic apparatus described in JP2012-139460A, for example, in a case where the user operates a predetermined switch, the detection result of the physical quantity is compared with the threshold value stored in the storage unit. As described above, in the ultrasound diagnostic apparatus described in JP2012-139460A, it is possible to check the polarization state of the piezoelectric element at the timing requested by the user (specifically, at the time of switch operation). In addition, in the ultrasound diagnostic apparatus described in JP2012-139460A, unlike in the apparatus described in JP2013-161955A, a polarization checking element other than the piezoelectric element for ultrasound diagnosis is not provided. Therefore, an increase in the size of the apparatus (specifically, an ultrasound probe) is suppressed.

The ultrasound diagnostic apparatus described in JP2012-139460A further has a high voltage application unit that applies a high voltage for repolarizing the piezoelectric element to the electrode of the piezoelectric element. Then, in a case where the physical quantity is equal to or less than the threshold value, a control signal is transmitted to the high voltage application unit, and a high voltage for repolarizing the piezoelectric element is applied to the electrode of the piezoelectric element. Therefore, in a case where the depolarization of the piezoelectric element progresses and the performance of the ultrasound probe is degraded, repolarization of the piezoelectric element can be performed. As a result, it is possible to cope with the depolarization of the piezoelectric element at an appropriate timing.

SUMMARY OF THE INVENTION

Incidentally, an ultrasound probe usually comprises a plurality of ultrasound transducers having piezoelectric elements. In addition, a physical quantity that changes with the degree of depolarization of the ultrasound transducer, for example, the voltage of the reception signal, tends to be different between elements because the driving time is different between the elements and the like. Therefore, in the case of determining the polarization state of the ultrasound transducer using the physical quantity (in other words, in the case of determining whether or not the polarization of the ultrasound transducer is required), it is necessary to take into consideration that the above-described physical quantity varies between piezoelectric elements. In the ultrasound diagnostic apparatus described in JP2012-139460A, however, since such a variation in physical quantity is not taken into consideration, there is a possibility that an appropriate determination result on the necessity of polarization cannot be obtained.

The invention has been made in view of the aforementioned circumstances, and it is an object of the invention to achieve the following goal. That is, it is an object of the invention to provide an ultrasound diagnostic apparatus and an operation method of an ultrasound diagnostic apparatus capable of obtaining an appropriate determination result on the necessity of polarization of ultrasound transducers even in a case where the degree of depolarization varies between the ultrasound transducers by solving the aforementioned problems in the related art.

In order to achieve the aforementioned object, an ultrasound diagnostic apparatus of the invention comprises: an ultrasound transducer unit that comprises a plurality of ultrasound transducers and transmits and receives ultrasound waves by driving driving target transducers, among the plurality of ultrasound transducers, inside a subject; a driving voltage supply unit that supplies a driving voltage to the driving target transducers; a checking operation unit that is operated to check a state of the ultrasound transducer unit; a controller that controls the driving voltage supply unit such that the driving voltage is supplied to each of the plurality of ultrasound transducers with all of the plurality of ultrasound transducers as the driving target transducers in a case where the checking operation unit is operated; a depolarization determination unit that, in a case where the checking operation unit is operated, calculates, for each ultrasound transducer, a reception sensitivity in a case where the ultrasound transducer unit receives an ultrasound wave with all of the plurality of ultrasound transducers as the driving target transducers, and determines whether or not a depolarization determination value calculated from the reception sensitivity of each ultrasound transducer satisfies numerical conditions set for the depolarization determination value; and a polarization voltage supply unit that supplies a polarization voltage to each of the plurality of ultrasound transducers in a case where the depolarization determination unit determines that the depolarization determination value satisfies the numerical conditions.

In the ultrasound diagnostic apparatus described above, it is preferable that the depolarization determination unit calculates at least one of a variance of the reception sensitivity of each ultrasound transducer, an average value of the reception sensitivity of each ultrasound transducer, or a minimum value of the reception sensitivity of each ultrasound transducer as the depolarization determination value.

In the ultrasound diagnostic apparatus described above, it is preferable that the ultrasound diagnostic apparatus further comprises a memory that stores a cumulative value of a driving time of the driving target transducer and that, in a case where the cumulative value stored in the memory is equal to or greater than a threshold value, the polarization voltage supply unit supplies the polarization voltage to each of the plurality of ultrasound transducers. In the ultrasound diagnostic apparatus described above, it is preferable that the cumulative value stored in the memory is set to an initial value after the polarization voltage supply unit supplies the polarization voltage to each of the plurality of ultrasound transducers. In the ultrasound diagnostic apparatus described above, it is preferable that a console is provided to receive a user's input operation regarding the threshold value. In the ultrasound diagnostic apparatus described above, it is preferable that the ultrasound transducer unit and the memory are provided in an ultrasound endoscope inserted into the subject. In the ultrasound diagnostic apparatus described above, it is preferable that the checking operation unit is provided in the ultrasound endoscope. In the ultrasound diagnostic apparatus described above, it is preferable that the ultrasound transducer unit is a convex type probe in which the plurality of ultrasound transducers are disposed in an arc shape.

In the ultrasound diagnostic apparatus described above, it is preferable that an operation mode of the ultrasound diagnostic apparatus includes a first mode and a second mode, the ultrasound transducer unit transmits and receives ultrasound waves to and from an inside of the subject while the operation mode is the first mode, the ultrasound transducer unit is located outside the subject while the operation mode is the second mode, the checking operation unit is operated while the operation mode is the second mode, and the polarization voltage supply unit supplies the polarization voltage to each of the plurality of ultrasound transducers while the operation mode is the second mode.

In the ultrasound diagnostic apparatus described above, the ultrasound transducer unit may have an acoustic matching layer disposed outside the plurality of ultrasound transducers. In a case where the checking operation unit is operated, the controller may control the driving voltage supply unit such that the ultrasound transducer unit transmits ultrasound waves with all of the plurality of ultrasound transducers as the driving target transducers and receive ultrasound waves reflected by the acoustic matching layer. Alternatively, in the ultrasound diagnostic apparatus described above, the checking operation unit may be operated in a state in which the ultrasound transducer unit is in contact with a phantom disposed outside the subject. In a case where the checking operation unit is operated, the controller may control the driving voltage supply unit such that the ultrasound transducer unit transmits ultrasound waves with all of the plurality of ultrasound transducers as the driving target transducers and receive ultrasound waves reflected by the phantom.

In addition, in order to achieve the object described above, an operation method of an ultrasound diagnostic apparatus of the invention comprises: by using an ultrasound transducer unit comprising a plurality of ultrasound transducers, transmitting and receiving ultrasound waves by driving target transducers, among the plurality of ultrasound transducers, inside a subject; by using a driving voltage supply unit, supplying a driving voltage to the driving target transducers; operating a checking operation unit to check a state of the ultrasound transducer unit; by using a controller, controlling the driving voltage supply unit such that the driving voltage is supplied to each of the plurality of ultrasound transducers with all of the plurality of ultrasound transducers as the driving target transducers in a case where the checking operation unit is operated; by using a depolarization determination unit, in a case where the checking operation unit is operated, calculating, for each ultrasound transducer, a reception sensitivity in a case where the ultrasound transducer unit receives an ultrasound wave with all of the plurality of ultrasound transducers as the driving target transducers, and determining whether or not a depolarization determination value calculated from the reception sensitivity of each ultrasound transducer satisfies numerical conditions set for the depolarization determination value; and by using a polarization voltage supply unit, supplying a polarization voltage to each of the plurality of ultrasound transducers in a case where the depolarization determination unit determines that the depolarization determination value satisfies the numerical conditions.

According to the ultrasound diagnostic apparatus and the operation method of the ultrasound diagnostic apparatus of the invention, even in a case where the degree of depolarization varies between ultrasound transducers, it is possible to obtain an appropriate determination result on the necessity of polarization of ultrasound transducers.

DESCRIPTION OF THE PREFERRED EMBODIMENTS

An ultrasound diagnostic apparatus according to an embodiment (the present embodiment) of the invention will be described in detail below with reference to preferred embodiments shown in the accompanying diagrams. The present embodiment is a representative embodiment of the invention, but is merely an example and does not limit the invention.

In addition, in this specification, the numerical range expressed by using "~" means a range including numerical values described before and after "~" as a lower limit and an upper limit.

<<Outline of Ultrasound Diagnostic Apparatus>>

Figure 1:
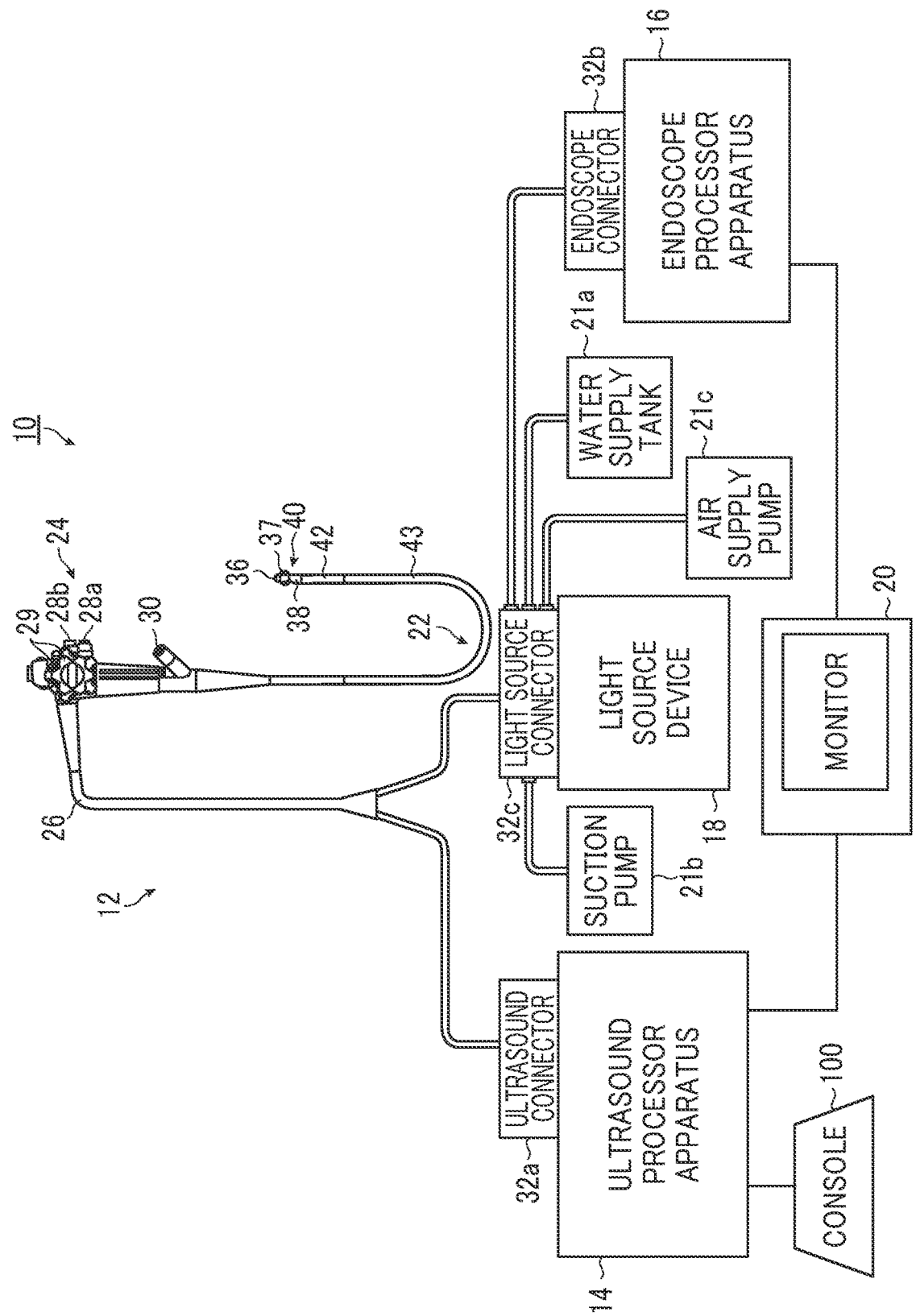
FIG. 1 is a diagram showing the schematic configuration of an ultrasound diagnostic apparatus according to an embodiment of the invention.
Figure 2:
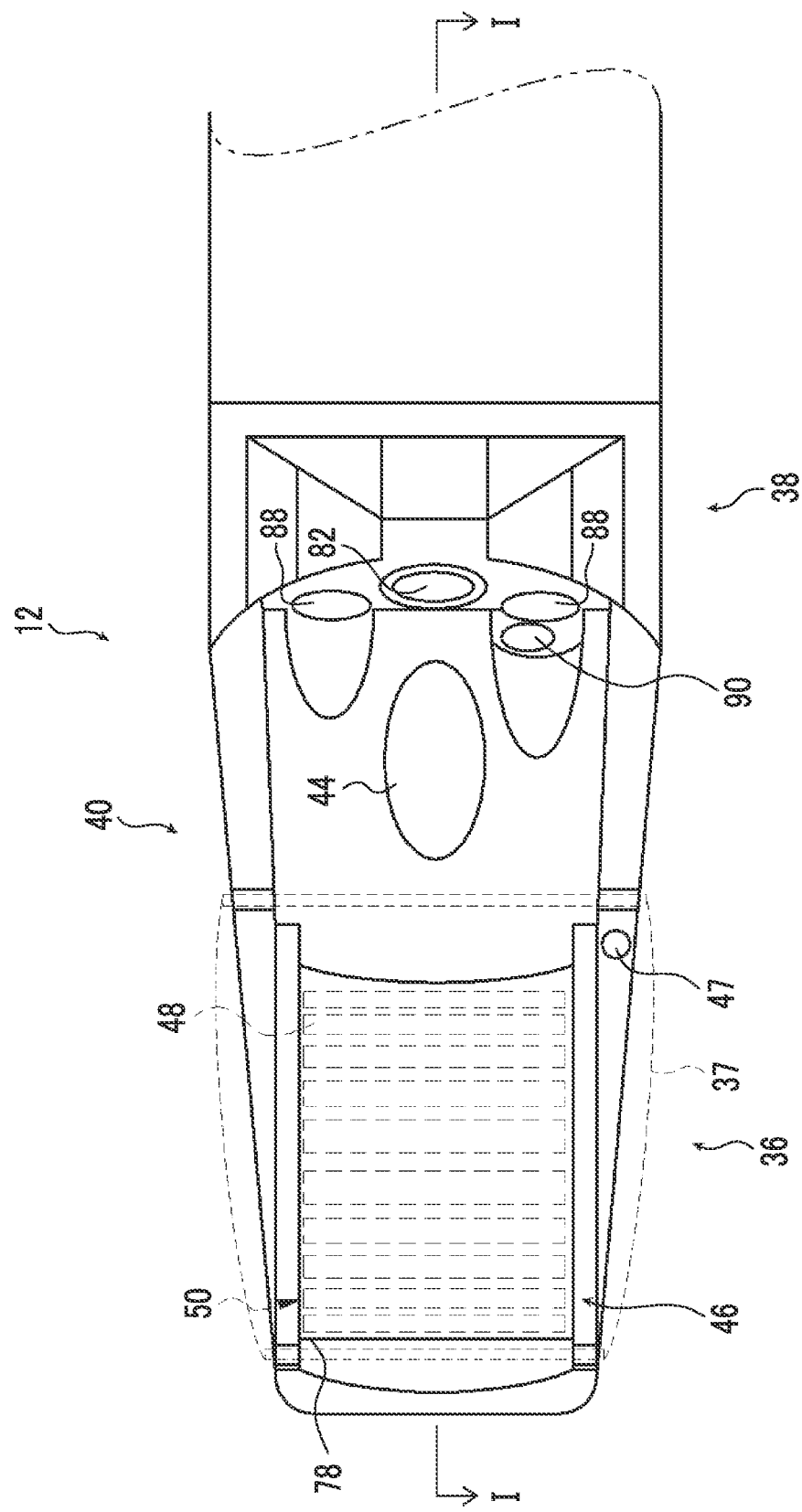
FIG. 2 is a plan view showing a distal end portion of an insertion part of an ultrasound endoscope and its periphery.
Figure 3:
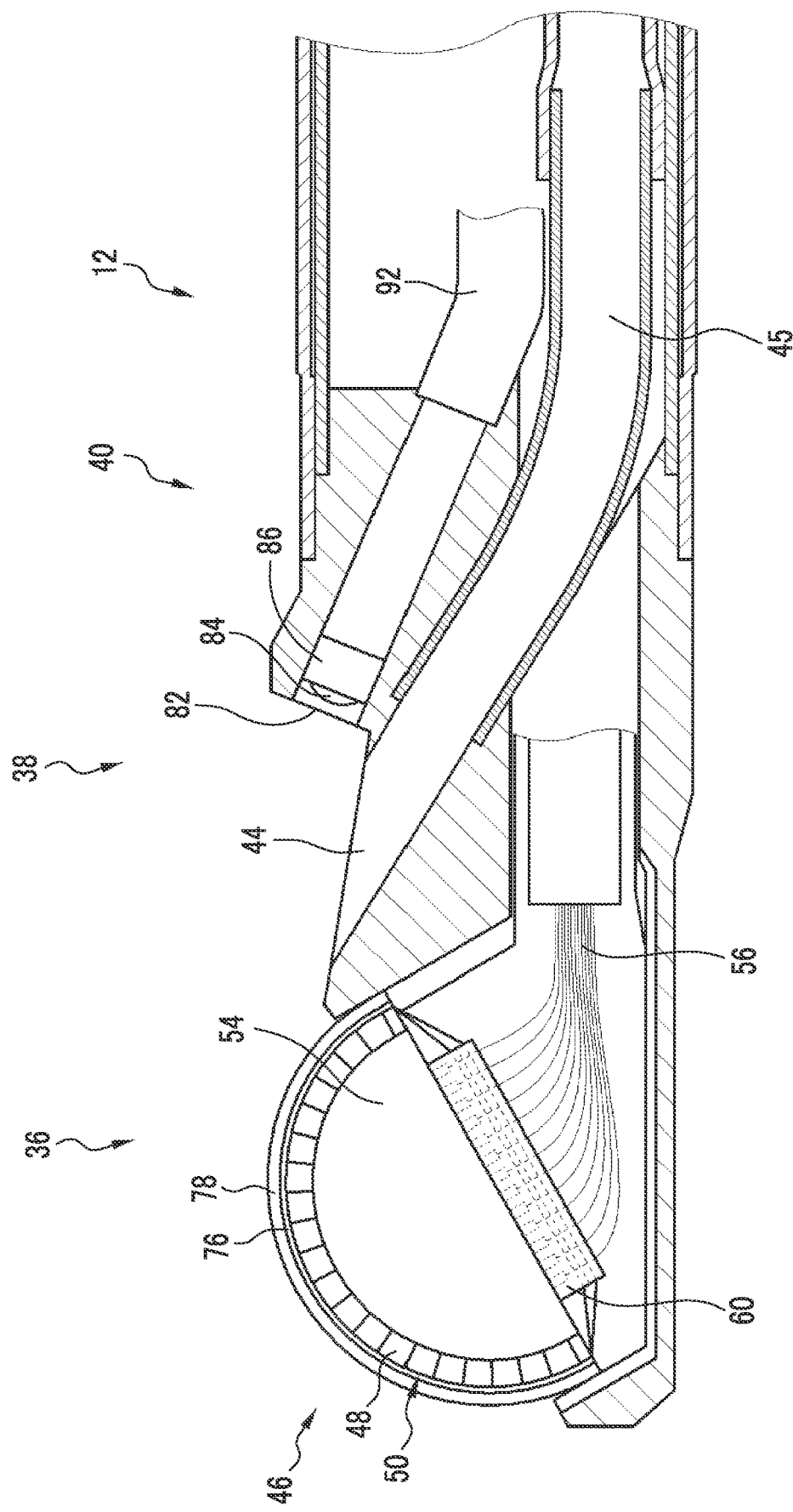
FIG. 3 is a diagram showing a cross section of the distal end portion of the insertion part of the ultrasound endoscope taken along the line I-I in FIG. 2.
Figure 4:
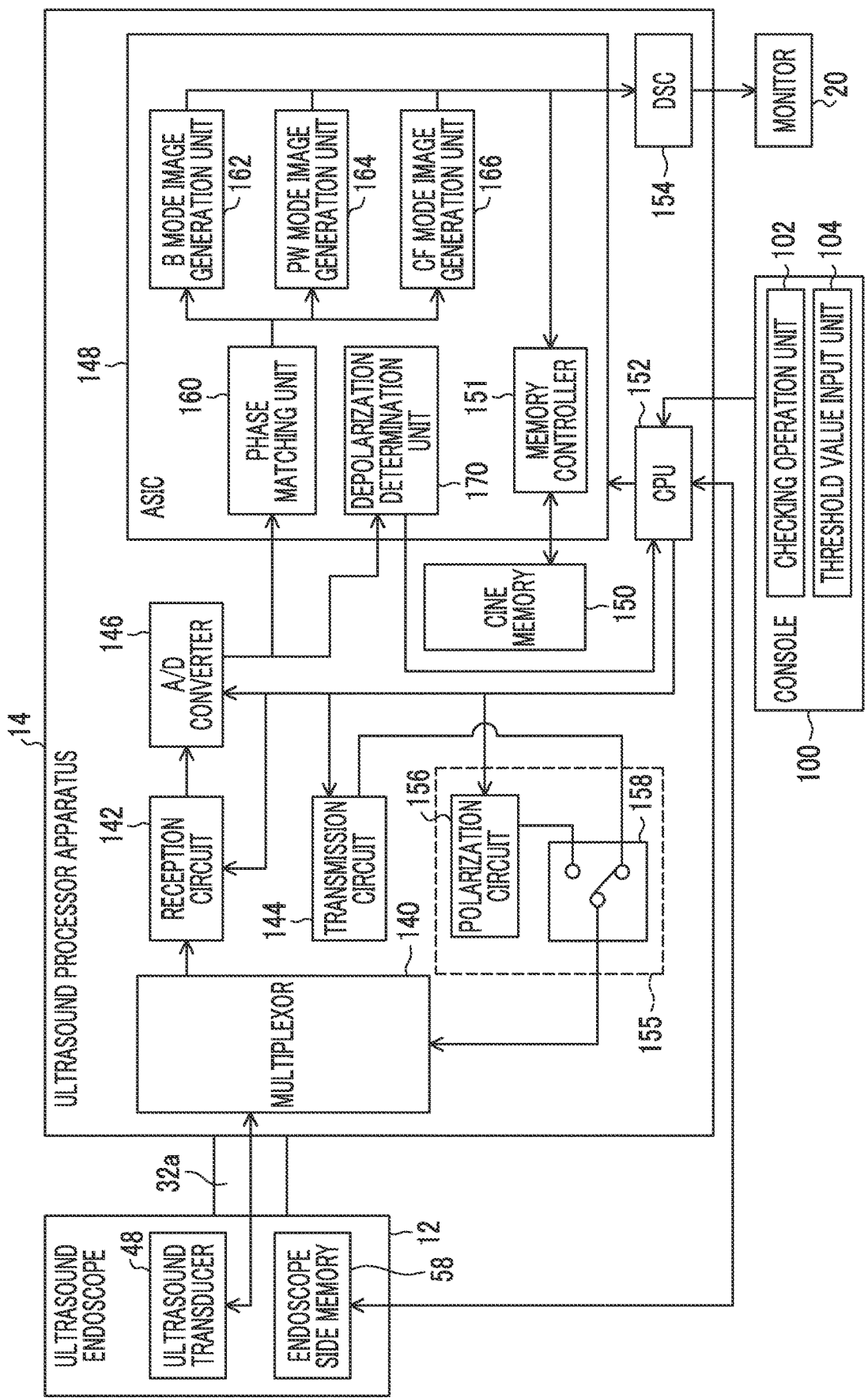
FIG. 4 is a block diagram showing the configurations of an ultrasound endoscope and an ultrasound processor apparatus.

The outline of an ultrasound diagnostic apparatus 10 according to the present embodiment will be described with reference to FIGS. 1 to 4. FIG. 1 is a diagram showing the schematic configuration of ultrasound diagnostic apparatus 10. FIG. 2 is an enlarged plan view showing a distal end portion of an insertion part 22 of an ultrasound endoscope 12 and the periphery thereof. In FIG. 2, for convenience of illustration, a balloon 37 to be described later is shown by a broken line. FIG. 3 is a diagram showing a cross section of a distal end portion 40 of the insertion part 22 of the ultrasound endoscope 12 taken along the line I-I in FIG. 2. FIG. 4 is a block diagram showing the configurations of the ultrasound endoscope 12 and an ultrasound processor apparatus 14.

The ultrasound diagnostic apparatus 10 is an ultrasound endoscope system, and is used to observe (hereinafter, also referred to as ultrasound diagnosis) the state of an observation target part in a body of a patient, who is a subject, using ultrasound waves. Here, the observation target part is a part that is difficult to examine from the body surface side (outside) of the patient, for example, a gallbladder or a pancreas. By using the ultrasound diagnostic apparatus 10, it is possible to perform ultrasound diagnosis of the state of the observation target part and the presence or absence of an abnormality through gastrointestinal tracts such as esophagus, stomach, duodenum, small intestine, and large intestine which are body cavities of the patient.

As shown in FIG. 1, the ultrasound diagnostic apparatus 10 has the ultrasound endoscope 12, the ultrasound processor apparatus 14, an endoscope processor apparatus 16, a light source device 18, a monitor 20, and a console 100. As shown in FIG. 1, a water supply tank 21a, a suction pump 21b, and an air supply pump 21c are provided as accessories of the ultrasound diagnostic apparatus 10. In addition, a pipe line (not shown) serving as a flow path of water and gas is formed in the ultrasound endoscope 12.

The ultrasound endoscope 12 is an endoscope, and as shown in FIG. 1, has the insertion part 22 to be inserted into the body cavity of a patient and an operation unit 24 operated by an operator (user), such as a doctor or a technician. In addition, as shown in FIGS. 2 and 3, an ultrasound transducer unit 46 comprising a plurality of ultrasound transducers 48 is attached to the distal end portion 40 of the insertion part 22.

By the function of the ultrasound endoscope 12, the operator can acquire an endoscope image of the inner wall of the body cavity of the patient and an ultrasound image of the observation target part. The endoscope image is an image obtained by imaging the inner wall of the body cavity of the patient using an optical method. The ultrasound image is an image obtained by receiving a reflected wave (echo) of an ultrasound wave transmitted from the inside of the body cavity of the patient to the observation target part and imaging the reception signal. The ultrasound endoscope 12 will be described in detail later.

As shown in FIG. 1, the ultrasound processor apparatus 14 is connected to the ultrasound endoscope 12 through a universal cord 26 and an ultrasound connector 32a provided at an end portion of the universal cord 26. The ultrasound processor apparatus 14 controls the ultrasound transducer unit 46 of the ultrasound endoscope 12 to transmit the ultrasound wave to the ultrasound transducer unit 46. In addition, the ultrasound processor apparatus 14 generates an ultrasound image by imaging the reception signal in a case where the reflected wave (echo) of the ultrasound wave is received by the ultrasound transducer unit 46. The ultrasound processor apparatus 14 will be described in detail later.

As shown in FIG. 1, the endoscope processor apparatus 16 is connected to the ultrasound endoscope 12 through the universal cord 26 and an endoscope connector 32b provided at an end portion of the universal cord 26. The endoscope processor apparatus 16 generates an endoscope image by acquiring image data of an observation target adjacent part imaged by the ultrasound endoscope 12 (more specifically, a solid-state imaging element 86 to be described later) and performing predetermined image processing on the acquired image data. The observation target adjacent part is a portion of the inner wall of the body cavity of the patient that is adjacent to the observation target part.

As shown in FIG. 1, the light source device 18 is connected to the ultrasound endoscope 12 through the universal cord 26 and a light source connector 32c provided at an end portion of the universal cord 26. The light source device 18 emits white light or specific wavelength light formed of three primary color light components of red light, green light, and blue light at the time of imaging the observation target adjacent part using the ultrasound endoscope 12. The light emitted from the light source device 18 propagates through the ultrasound endoscope 12 through a light guide (not shown) included in the universal cord 26, and is emitted from the ultrasound endoscope 12 (more specifically, an illumination window 88 to be described later). As a result, the observation target adjacent part is illuminated with the light from the light source device 18.

In the present embodiment, the ultrasound processor apparatus 14 and the endoscope processor apparatus 16 are formed by two apparatuses (computers) provided separately. However, the invention is not limited thereto, and both the ultrasound processor apparatus 14 and the endoscope processor apparatus 16 may be formed by one apparatus.

As shown in FIG. 1, the monitor 20 is connected to the ultrasound processor apparatus 14, and the endoscope processor apparatus 16, and displays an ultrasound image generated by the ultrasound processor apparatus 14 and an endoscope image generated by the endoscope processor apparatus 16. Regarding the display of the ultrasound image and the endoscope image, either one of the images may be switched and displayed on the monitor 20, or both the images may be displayed at the same time. A configuration may be adopted in which these display methods can be freely selected and changed. In the present embodiment, the ultrasound image and the endoscope image are displayed on one monitor 20. However, a monitor for displaying the ultrasound image and a monitor for displaying the endoscope image may be separately provided. In addition, the ultrasound image and the endoscope image may be displayed in a display form other than the monitor 20. For example, the ultrasound image and the endoscope image may be displayed on a display of a personal terminal carried by the operator.

The console 100 is an input device provided for the operator to input information necessary for ultrasound diagnosis or for the operator to instruct the ultrasound processor apparatus 14 to start ultrasound diagnosis. The console 100 is configured to include, for example, a keyboard, a mouse, a trackball, a touch pad, and a touch panel, and is connected to a CPU 152 of the ultrasound processor apparatus 14 as shown in FIG. 4. In a case where the console 100 is operated, the CPU 152 of the ultrasound processor apparatus 14 controls each unit of the apparatus (for example, a reception circuit 142 and a transmission circuit 144 to be described later) according to the operation content.

Specifically, the operator inputs examination information (for example, examination order information including a date and an order number and patient information including a patient ID and a patient name) through the console 100 before starting the ultrasound diagnosis. In a case where the operator gives an instruction to start the ultrasound diagnosis through the console 100 after the input of the examination information is completed, the CPU 152 of the ultrasound processor apparatus 14 controls each unit of the ultrasound processor apparatus 14 so that the ultrasound diagnosis is performed based on the input examination information.

The operator can set various control parameters with the console 100 at the time of performing the ultrasound diagnosis. As the control parameters, for example, selection results of a live mode and a freeze mode, set values of the display depth (depth), selection results of an ultrasound image generation mode, and the like can be mentioned. Here, the "live mode" is a mode in which ultrasound images (moving images) obtained at a predetermined frame rate are sequentially displayed (displayed in real time). The "freeze mode" is a mode in which an ultrasound image (still image) of one frame acquired in the past is read out from a cine memory 150 to be described later and displayed.

There are a plurality of ultrasound image generation modes that can be selected in the present embodiment. Specifically, there are a brightness (B) mode, a color flow (CF) mode, and a pulse wave (PW) mode. The B mode is a mode in which a tomographic image is displayed by converting the amplitude of the ultrasound echo into a brightness. The CF mode is a mode in which average blood flow speed, flow fluctuation, strength of flow signal, flow power, and the like are mapped to various colors and displayed so as to be superimposed on a B mode image. The PW mode is a mode in which the speed (for example, blood flow speed) of the ultrasound echo source detected based on the transmission and reception of the pulse wave is displayed. The ultrasound image generation modes described above are merely examples, and modes other than the above-described three kinds of modes, for example, an amplitude (A) mode and a motion (M) mode may be further included.

In the present embodiment, a checking operation unit 102 and a threshold value input unit 104 are provided in the console 100 as shown in FIG. 4. The checking operation unit 102 is a unit operated by the operator in order to check the state of the ultrasound endoscope 12, in particular, the state of the ultrasound transducer unit 46. Here, the state of the ultrasound transducer unit 46 is a state relevant to the performance of the ultrasound transducer unit 46, specifically, the degree of progress of depolarization of the ultrasound transducer unit 46. The checking operation unit 102 may be a physical push button or switch provided in the console 100, or may be a button image drawn on the display screen of the console 100 in a case where the console 100 is formed by a touch pad or a touch panel.

The threshold value input unit 104 is a unit operated by the operator in order to set a threshold value used for determining whether or not polarization processing is required, which will be described later. That is, the console 100 comprising the threshold value input unit 104 receives an input operation of the operator regarding the above-described threshold value. The threshold value input unit 104 may be formed by a keyboard, a numeric keypad, or a mouse provided in the console 100. Alternatively, the threshold value input unit 104 may be formed by an input window or an input box drawn on the display screen of the console 100 in a case where the console 100 is formed by a touch pad or a touch panel.

In the ultrasound diagnostic apparatus 10 configured as described above, in a case where the electric power is supplied, the operator first operates the console 100 to input the above-described examination information.

In a case where the operator gives an instruction to start the ultrasound diagnosis through the console 100 after the input of the examination information is completed, the operation mode of the ultrasound diagnostic apparatus 10 (hereinafter, simply referred to as an operation mode) is switched to the first mode. Thereafter, the operator inserts the insertion part 22 of the ultrasound endoscope 12 into the body cavity of the patient. As a result, a plurality of ultrasound transducers 48 provided in the ultrasound transducer unit 46 are disposed in the body cavity of the patient. While the operation mode is the first mode, a diagnostic step is performed. In the diagnostic step, ultrasound diagnosis is performed by the ultrasound diagnostic apparatus 10. That is, while the operation mode is the first mode, each of the ultrasound image and the endoscope image is acquired according to the examination information.

On the other hand, until the operator gives an instruction to start the ultrasound diagnosis after the electric power is supplied, the operation mode is set to the second mode. In the present embodiment, while the operation mode is the second mode, the ultrasound endoscope 12 including the ultrasound transducer unit 46 is located outside the body cavity of the patient (that is, outside the patient). Then, while the operation mode is the second mode, a scope checking step is performed. In the scope checking step, the state of the ultrasound endoscope 12, in particular, the state of the ultrasound transducer unit 46 is checked, and the necessity of polarization of the ultrasound transducer 48 is determined from the checking result. In a case where the determination result that the polarization is required is obtained, the ultrasound processor apparatus 14 performs polarization processing for polarizing (repolarizing) the ultrasound transducer 48.

The polarization processing is processing for polarizing (repolarizing) the ultrasound transducer 48 by supplying a polarization voltage to the ultrasound transducer 48. By performing the polarization processing, the depolarized ultrasound transducer 48 can be polarized again by repeating the ultrasound diagnosis. As a result, it is possible to restore the reception sensitivity of the ultrasound transducer 48 with respect to ultrasound waves to a satisfactory level.

As described above, in the present embodiment, the operation mode includes the first mode and the second mode. However, the operation mode is not limited to the above-described modes, and may include at least the first mode and the second mode, and modes (for example, a mode for maintenance of each unit of the ultrasound diagnostic apparatus 10) other than the above-described modes may be further included.

<<Configuration of Ultrasound Endoscope>>

Next, the configuration of the ultrasound endoscope 12 will be described with reference to FIGS. 1 to 4. As shown in FIG. 1, the ultrasound endoscope 12 has the insertion part 22 and the operation unit 24. As shown in FIG. 1, the insertion part 22 comprises the distal end portion 40, a bending portion 42, and a flexible portion 43 in order from the distal end side (free end side). As shown in FIG. 2, an ultrasound observation portion 36 and an endoscope observation portion 38 are provided in the distal end portion 40.

As shown in FIGS. 2 and 3, a treatment tool lead-out port 44 is provided in the distal end portion 40. The treatment tool lead-out port 44 serves as an outlet of a treatment tool (not shown), such as forceps, an insertion needle, or a high frequency scalpel, and also serves as a suction port for sucking aspirates, such as blood and body waste.

As shown in FIG. 2, a cleaning nozzle 90 formed to clean the surfaces of an observation window 82 and the illumination window 88 is provided in the distal end portion 40. Air or cleaning liquid is ejected from the cleaning nozzle 90 toward the observation window 82 and the illumination window 88.

As shown in FIGS. 1 and 2, a balloon 37 that can expand and contract is attached to the distal end portion 40 at a position covering the ultrasound transducer unit 46. The balloon 37 can be inserted into the body cavity of the patient together with the ultrasound transducer unit 46. Then, water (specifically, degassed water) as an ultrasound transmission medium is injected into the balloon 37 from a water supply port 47 formed near the ultrasound transducer unit 46 in the distal end portion 40. As a result, the balloon 37 expands. In a case where the expanded balloon 37 comes in contact with the inner wall of the body cavity (for example, the periphery of the observation target adjacent part), air between the ultrasound transducer unit 46 and inner wall of the body cavity is eliminated. Therefore, it is possible to prevent attenuation of ultrasound waves and reflected waves (echoes) thereof in the air.

As shown in FIG. 1, the bending portion 42 is a portion provided on the more proximal side (side opposite to the side where the ultrasound transducer unit 46 is provided) than the distal end portion 40 in the insertion part 22, and can bend freely. As shown in FIG. 1, the flexible portion 43 is a portion connecting the bending portion 42 and the operation unit 24 to each other, has flexibility, and is provided so as to extend in an elongated state.

As shown in FIG. 1, a pair of angle knobs 29 and a treatment tool insertion port 30 are provided in the operation unit 24. In a case where each angle knob 29 is rotated, the bending portion 42 is remotely operated to be bent and deformed. By this deformation operation, the distal end portion 40 of the insertion part 22 in which the ultrasound observation portion 36 and the endoscope observation portion 38 are provided can be directed in a desired direction. The treatment tool insertion port 30 is a hole formed to insert a treatment tool, such as forceps, and communicates with the treatment tool lead-out port 44 through a treatment tool channel 45 (refer to FIG. 3).

As shown in FIG. 1, an air and water supply button 28*a* for opening and closing an air and water supply pipe line (not shown) extending from the water supply tank 21*a*, and a suction button 28*b* for opening and closing a suction pipe line (not shown) extending from the suction pump 21*b* are provided in the operation unit 24. Gas, such as air sent from the air supply pump 21*c* and water in the water supply tank 21*a* flow through the air and water supply pipe line. In a case where the air and water supply button 28*a* is operated, a portion to be opened in the air and water supply pipe line is switched, and gas and water injection ports are also switched between the cleaning nozzle 90 and the water supply port 47 in a corresponding manner. That is, it is possible to selectively perform cleaning of the endoscope observation portion 38 and expansion of the balloon 37 by operating the air and water supply button 28*a*.

The suction pipe line is provided to suck an aspirate in the body cavity sucked from the cleaning nozzle 90 or to suck water in the balloon 37 through the water supply port 47. In a case where the suction button 28*b* is operated, a portion to be opened in the suction pipe line is switched, and a suction port is also switched between the cleaning nozzle 90 and the water supply port 47 in a corresponding manner. That is, a target object to be sucked by the suction pump 21*b* can be switched by operating the suction button 28*b*.

As shown in FIG. 1, the ultrasound connector 32*a* connected to the ultrasound processor apparatus 14, the endoscope connector 32*b* connected to the endoscope processor apparatus 16, and the light source connector 32*c* connected to the light source device 18 are provided in the other end portion of the universal cord 26. The ultrasound endoscope 12 is detachably connected to the ultrasound processor apparatus 14, the endoscope processor apparatus 16, and the light source device 18 through the connectors 32*a*, 32*b*, and 32*c*, respectively.

Next, the ultrasound observation portion 36 and the endoscope observation portion 38 among the components of the ultrasound endoscope 12 will be described in detail.

(Ultrasound Observation Portion)

The ultrasound observation portion 36 is a portion provided to acquire an ultrasound image, and is disposed on the distal end side in the distal end portion 40 of the insertion part 22 as shown in FIGS. 2 and 3. As shown in FIG. 3, the ultrasound observation portion 36 comprises the ultrasound transducer unit 46, a plurality of coaxial cables 56, and a flexible printed circuit (FPC) 60.

The ultrasound transducer unit 46 corresponds to an ultrasound probe (probe), and transmits and receives ultrasound waves in the body cavity of the patient (inside the subject). Specifically, the ultrasound transducer unit 46 transmits and receives ultrasound waves by driving a driving target transducer, among the plurality of ultrasound transducers 48, in the body cavity of the patient. The driving target transducer is the ultrasound transducer 48 that is actually driven (vibrated) at the time of ultrasound diagnosis to emit an ultrasound wave and outputs a reception signal that is an electric signal at the time of receiving the reflected wave (echo). In the present embodiment, the ultrasound transducer unit 46 is integrated with the endoscope, so that the ultrasound transducer unit 46 is inserted into the body cavity of the patient together with the endoscope. However, the invention is not limited thereto. For example, the ultrasound transducer unit 46 may be separated from the endoscope, so that the ultrasound transducer unit 46 is inserted into the body cavity of the patient separately from the endoscope.

As shown in FIG. 3, the ultrasound transducer unit 46 according to the present embodiment is a convex type probe in which a plurality of ultrasound transducers 48 are disposed in an arc shape, and transmits ultrasound waves in a radial shape (arc shape). However, the type (model) of the ultrasound transducer unit 46 is not particularly limited, and other types may be used as long as it is possible to transmit and receive ultrasound waves. For example, a sector type, a linear type, and a radial type may be used.

As shown in FIG. 3, the ultrasound transducer unit 46 is formed by laminating a backing material layer 54, an ultrasound transducer array 50, an acoustic matching layer 76, and an acoustic lens 78.

The ultrasound transducer array 50 includes a plurality of ultrasound transducers 48 (ultrasound transducers) arranged in a one-dimensional array as shown in FIG. 3. More specifically, the ultrasound transducer array 50 is formed by arranging N (for example, N=128) ultrasound transducers 48 at equal intervals in a convex bending shape along the axial direction of the distal end portion 40 (longitudinal axis direction of the insertion part 22). The ultrasound transducer array 50 may be one in which a plurality of ultrasound transducers 48 are disposed in a two-dimensional array.

Each of the N ultrasound transducers 48 is formed by disposing electrodes on both surfaces of a single crystal transducer that is a piezoelectric element. As the single crystal transducer, any of quartz, lithium niobate, lead magnesium niobate (PMN), lead zinc niobate (PZN), lead indium niobate (PIN), lead titanate (PT), lithium tantalate, langasite, and zinc oxide can be used. The electrodes is an individual electrode (not shown) individually provided for each of the plurality of ultrasound transducers 48 and a ground electrode (not shown) common to the plurality of ultrasound transducers 48. In addition, the electrodes are electrically connected to the ultrasound processor apparatus 14 through the coaxial cable 56 and the FPC 60.

The ultrasound transducer 48 according to the present embodiment needs to be driven (vibrated) at a relatively high frequency of 7 MHz to 8 MHz level in order to acquire an ultrasound image in the body cavity of the patient. For this reason, the thickness of the piezoelectric element forming the ultrasound transducer 48 is designed to be relatively small. For example, the thickness of the piezoelectric element forming the ultrasound transducer 48 is 75 µm to 125 µm, preferably 90 µm to 125 µm.

A pulsed driving voltage is supplied from the ultrasound processor apparatus 14 to each ultrasound transducer 48, as an input signal, through the coaxial cable 56. In a case where the driving voltage is applied to the electrodes of the ultrasound transducer 48, the piezoelectric element expands and contracts to drive (vibrate) the ultrasound transducer 48.

As a result, a pulsed ultrasound wave is output from the ultrasound transducer 48. In this case, the amplitude of the ultrasound wave output from the ultrasound transducer 48 has a magnitude corresponding to the intensity (output intensity) in a case where the ultrasound transducer 48 outputs the ultrasound wave. Here, the output intensity is defined as the magnitude of the sound pressure of the ultrasound wave output from the ultrasound transducer 48.

Each ultrasound transducer 48 vibrates (is driven) upon receiving the reflected wave (echo) of the ultrasound wave, and the piezoelectric element of each ultrasound transducer 48 generates an electric signal. The electric signal is output from each ultrasound transducer 48 to the ultrasound processor apparatus 14 as a reception signal of the ultrasound wave. In this case, the magnitude (voltage value) of the electric signal output from the ultrasound transducer 48 has a magnitude corresponding to the reception sensitivity in a case where the ultrasound transducer 48 receives the ultrasound wave. Here, the reception sensitivity is defined as a ratio of the amplitude of the electric signal, which is output from the ultrasound transducer 48 in response to reception of the ultrasound wave, to the amplitude of the ultrasound wave transmitted by the ultrasound transducer 48.

As described above, the ultrasound transducer unit 46 of the present embodiment is a convex type. That is, in the present embodiment, by sequentially driving the N ultrasound transducers 48 provided in the ultrasound transducer unit 46 with an electronic switch such as a multiplexer 140, an ultrasound scan occurs in a scanning range along the curved surface on which the ultrasound transducer array 50 is disposed, for example, in the range of about several tens of mm from the center of curvature of the curved surface.

More specifically, for example, in the case of acquiring a B mode image (tomographic image) as an ultrasound image, a driving voltage is supplied to m (for example, m=N/2) driving target transducers arranged in series, among the N ultrasound transducers 48, by channel selection of the multiplexer 140. As a result, each of the m driving target transducers is driven, and an ultrasound wave from each of the driving target transducers is output through the opening. The output m ultrasound waves are immediately synthesized, and the composite wave (ultrasound beam) is transmitted to the observation target part. Thereafter, each of the m driving target transducers receives an ultrasound wave (echo) reflected at the observation target part, and outputs an electric signal (reception signal) corresponding to the reception sensitivity at that point in time.

The above-described series of steps (that is, supply of a driving voltage, transmission and reception of ultrasound waves, and output of an electric signal) are repeatedly performed while switching the opening channel in the multiplexer 140 to shift the position of the driving target transducer one by one (one ultrasound transducer 48 at a time). For example, in the case of acquiring a B mode image for one frame, the above-described series of steps (hereinafter, referred to as a path for convenience) are repeated a total of N times from the ultrasound transducer 48 on one end side toward the ultrasound transducer 48 on the other end side among the N ultrasound transducers 48, and each image piece forming the B mode image is formed by each path. Here, the image piece is obtained by dividing an approximately fan-shaped B mode image into N equal parts along an arc which is the outer edge thereof.

As shown in FIG. 3, the backing material layer 54 supports the ultrasound transducer array 50 from the back side (side opposite to the acoustic matching layer 76). In addition, the backing material layer 54 has a function of attenuating ultrasound waves propagating to the back side of the ultrasound transducer array 50 among ultrasound waves emitted from the ultrasound transducer 48 or ultrasound waves (echoes) reflected by the observation target part. The backing material is a material having rigidity, such as hard rubber, and an appropriate amount of ultrasound damping material (ferrite, ceramics, and the like) is added.

The acoustic matching layer 76 is provided for acoustic impedance matching between the body of the patient and the driving target transducer. The acoustic matching layer 76 is disposed outside the ultrasound transducer array 50 (that is, outside the plurality of ultrasound transducers 48). Strictly speaking, the acoustic matching layer 76 is superimposed on the ultrasound transducer array 50 as shown in FIG. 3. Since the acoustic matching layer 76 is provided, it is possible to increase the transmittance of the ultrasound wave. As a material of the acoustic matching layer 76, it is possible to use various organic materials whose acoustic impedance values are closer to that of the body of the patient than the piezoelectric element of the ultrasound transducer 48. Specific examples of the material of the acoustic matching layer 76 include epoxy resin, silicone rubber, polyimide, polyethylene, and the like.

Some of the ultrasound waves transmitted from the driving target transducers are reflected at the boundary position of the acoustic lens 78 due to the difference in acoustic impedance. Therefore, the ultrasound transducer unit 46 receives ultrasound waves reflected at the boundary position of the acoustic lens 78 with the driving target transducers. At this time, each of the driving target transducers receives the ultrasound wave with the reception sensitivity at that point in time, and outputs the reception signal corresponding to the reception sensitivity.

The acoustic lens 78 converges the ultrasound waves emitted from the driving target transducers toward the observation target part, and is superimposed on the acoustic matching layer 76 as shown in FIG. 3. The acoustic lens 78 is formed of, for example, silicon resin (millable silicone rubber (HTV rubber), liquid silicone rubber (RTV rubber), and the like), butadiene resin, and polyurethane resin, and powders of titanium oxide, alumina, silica, and the like are mixed as necessary.

The FPC 60 is electrically connected to the electrode of each ultrasound transducer 48. As shown in FIG. 3, each of the plurality of coaxial cables 56 is wired to the FPC 60 at one end thereof. In a case where the ultrasound endoscope 12 is connected to the ultrasound processor apparatus 14 through the ultrasound connector 32a, each coaxial cable 56 is electrically connected to the ultrasound processor apparatus 14 at the other end (side opposite to the FPC 60).

As shown in FIG. 4, the ultrasound endoscope 12 comprises a memory (hereinafter, referred to as an endoscope side memory 58). The endoscope side memory 58 stores a cumulative value of the driving time of the driving target transducer (that is, the total driving time) in a period during which the operation mode is the first mode. In the present embodiment, it is assumed that the time from the operator's instruction to start ultrasound diagnosis to the end of the ultrasound diagnosis (more specifically, the time during which ultrasound diagnosis is performed in the live mode) is handled as the driving time. However, the invention is not limited thereto, and the time during which the driving voltage is actually supplied to the driving target transducer may be the driving time.

In a state in which the ultrasound endoscope 12 is connected to the ultrasound processor apparatus 14, the CPU 152 of the ultrasound processor apparatus 14 can access the endoscope side memory 58 to read the cumulative value of the driving time stored in the endoscope side memory 58. In addition, the CPU 152 of the ultrasound processor apparatus 14 rewrites (that is, clears) the cumulative value of the driving time stored in the endoscope side memory 58 to an initial value, or updates the cumulative value of the driving time in a case where the cumulative value of the driving time increases with the execution of the ultrasound diagnosis.

(Endoscope Observation Portion)

The endoscope observation portion 38 is a portion provided to acquire an endoscope image, and is disposed on the more proximal end side than the ultrasound observation portion 36 in the distal end portion 40 of the insertion part 22 as shown in FIGS. 2 and 3. As shown in FIGS. 2 and 3, the endoscope observation portion 38 includes the observation window 82, an objective lens 84, the solid-state imaging element 86, the illumination window 88, the cleaning nozzle 90, a wiring cable 92, and the like.

As shown in FIG. 3, the observation window 82 is attached so as to be inclined with respect to the axial direction (longitudinal axis direction of the insertion part 22) at the distal end portion 40 of the insertion part 22. Light incident through the observation window 82 and reflected at the observation target adjacent part is focused on the imaging surface of the solid-state imaging element 86 by the objective lens 84.

The solid-state imaging element 86 photoelectrically converts the reflected light of the observation target adjacent part, which is focused on the imaging surface after being transmitted through the observation window 82 and the objective lens 84, and outputs an imaging signal. As the solid-state imaging element 86, it is possible to use a charge coupled device (CCD), a complementary metal oxide semiconductor (CMOS), and the like. The captured image signal output from the solid-state imaging element 86 is transmitted to the endoscope processor apparatus 16 by the universal cord 26 through the wiring cable 92 extending from the insertion part 22 to the operation unit 24.

As shown in FIG. 2, the illumination window 88 is provided at both side positions of the observation window 82. An exit end of a light guide (not shown) is connected to the illumination window 88. The light guide extends from the insertion part 22 to the operation unit 24, and its incidence end is connected to the light source device 18 connected through the universal cord 26. The illumination light emitted from the light source device 18 is transmitted through the light guide and is emitted from the illumination window 88 toward the observation target adjacent part.

<<Configuration of Ultrasound Processor Apparatus>>

The ultrasound processor apparatus 14 causes the ultrasound transducer unit 46 to transmit and receive ultrasound waves, and generates an ultrasound image by converting the reception signal, which is output from the driving target transducer at the time of ultrasound wave reception, into an image. In addition, the ultrasound processor apparatus 14 displays the generated ultrasound image on the monitor 20.

In the present embodiment, the ultrasound processor apparatus 14 (strictly speaking, a polarization processing unit 155 to be described below) performs polarization processing, and supplies a polarization voltage to each ultrasound transducer 48 to perform polarization (repolarization). By the execution of the polarization processing, the depolarized ultrasound transducer 48 can be polarized again by repeating the ultrasound diagnosis. As a result, it is possible to restore the reception sensitivity of the ultrasound transducer 48 with respect to ultrasound waves to a satisfactory level.

In the present embodiment, the polarization processing is performed in a period during which the ultrasound diagnosis is not performed, specifically, a period during which the operation mode is the second mode. More specifically, the polarization processing is performed in the scope checking step.

As shown in FIG. 4, the ultrasound processor apparatus 14 has the multiplexer 140, the reception circuit 142, the transmission circuit 144, an A/D converter 146, an Application Specific Integrated Circuit (ASIC) 148, the cine memory 150, a memory controller 151, a central processing unit (CPU) 152, a digital scan converter (DSC) 154, and the polarization processing unit 155.

As shown in FIG. 4, the reception circuit 142 and the transmission circuit 144 are electrically connected to the ultrasound transducer array 50 of the ultrasound endoscope 12 through the multiplexer 140. The multiplexer 140 selects a maximum of m driving target transducers from the N ultrasound transducers 48, and opens their channels.

The transmission circuit 144 forms a driving voltage supply unit, and is a circuit that supplies a driving voltage for ultrasound wave transmission to the driving target transducers selected by the multiplexer 140 in order to transmit ultrasound waves from the ultrasound transducer unit 46. The driving voltage is a pulsed voltage signal, and is applied to the electrodes of the driving target transducers through the universal cord 26 and the coaxial cable 56.

The reception circuit 142 is a circuit that receives an electric signal output from the driving target transducer that has received an ultrasound wave (echo), that is, a reception signal. In addition, according to the control signal transmitted from the CPU 152, the reception circuit 142 amplifies the reception signal received from the ultrasound transducer 48 and transmits the amplified signal to the A/D converter 146. As shown in FIG. 4, the A/D converter 146 is connected to the reception circuit 142, and converts the reception signal received from the reception circuit 142 from an analog signal to a digital signal and outputs the converted digital signal to the ASIC 148.

As shown in FIG. 4, the ASIC 148 is connected to the A/D converter 146. As shown in FIG. 4, the ASIC 148 forms a phase matching unit 160, a B mode image generation unit 162, a PW mode image generation unit 164, a CF mode image generation unit 166, and a depolarization determination unit 170. In the present embodiment, the above-described functions (specifically, the phase matching unit 160, the B mode image generation unit 162, the PW mode image generation unit 164, the CF mode image generation unit 166, and the depolarization determination unit 170) are realized by a hardware circuit, such as the ASIC 148. However, the invention is not limited thereto. The above-described functions may be realized by making the central processing unit (CPU) and software (computer program) for executing various kinds of data processing cooperate with each other.

The phase matching unit 160 performs processing for phasing addition (addition after matching the phases of reception data) by giving a delay time to the reception signal (reception data) digitized by the A/D converter 146. By the phasing addition processing, a sound ray signal with narrowed focus of the ultrasound echo is generated.

The B mode image generation unit 162, the PW mode image generation unit 164, and the CF mode image generation unit 166 generate an ultrasound image based on the electric signal (strictly speaking, the sound ray signal generated by phasing and adding the reception data) that is output from the driving target transducer among the plurality of ultrasound transducers 48 in a case where the ultrasound transducer unit 46 receives the ultrasound wave.

The B mode image generation unit 162 generates a B mode image that is a tomographic image of the inside of the patient (inside of the body cavity). For the sequentially generated sound ray signals, the B mode image generation unit 162 corrects the attenuation due to the propagation distance according to the depth of the reflection position of the ultrasound wave by sensitivity time gain control (STC). The B mode image generation unit 162 performs envelope detection processing and logarithm (Log) compression processing on the corrected sound ray signal, thereby generating a B mode image (image signal).

The PW mode image generation unit 164 generates an image showing the blood flow speed in a predetermined direction. The PW mode image generation unit 164 extracts a frequency component by applying a fast Fourier transform to a plurality of sound ray signals in the same direction among the sound ray signals sequentially generated by the phase matching unit 160. Thereafter, the PW mode image generation unit 164 calculates the blood flow speed from the extracted frequency component, and generates a PW mode image (image signal) showing the calculated blood flow speed.

The CF mode image generation unit 166 generates an image showing blood flow information in a predetermined direction. The CF mode image generation unit 166 generates an image signal indicating the blood flow information by calculating the autocorrelation between a plurality of sound ray signals in the same direction among the sound ray signals sequentially generated by the phase matching unit 160. Thereafter, the CF mode image generation unit 166 generates a CF mode image (image signal) as a color image on which the blood flow information is superimposed by including the image signal in the B mode image signal.

The number of ultrasound transducers 48 as driving target transducers in each image forming mode, the driving frequency, and the like are determined according to the type of the ultrasound image forming mode. For example, in order to generate an image for one frame (B mode image) in the B mode, all of the N ultrasound transducers 48 are used as driving target transducers. However, among the N ultrasound transducers 48, the driving frequency in the ultrasound transducer 48 on the end side is higher than that in the ultrasound transducer 48 in the vicinity of the center.

In the PW mode, since the ultrasound transducer 48 corresponding to the direction designated by the operator is used as a driving target transducer, the driving frequency of the ultrasound transducer 48 is higher than the driving frequency of the other ultrasound transducers 48. In the CF mode, in the case of generating the above-described color image (CF mode image), all of the N ultrasound transducers 48 are used as driving target transducers, but a larger number of ultrasound transducers 48 corresponding to the direction designated by the operator are driven. Therefore, in the CF mode, the driving frequency in the ultrasound transducer 48 on the end side is higher than that in the ultrasound transducer 48 in the vicinity of the center, and the driving frequency of the ultrasound transducer 48 corresponding to the direction designated by the operator is higher than the driving frequency of the other ultrasound transducers 48.

As described above, the number of driving target transducers and the driving frequency are changed according to the type of the ultrasound image forming mode. Due to this, the driving frequency (in other words, the driving time) of each ultrasound transducer 48 varies between the ultrasound transducers 48. As the driving time passes, depolarization proceeds in the ultrasound transducer 48. That is, the variation in the driving time between the ultrasound transducers 48 means that the degree of progress of depolarization varies between the ultrasound transducers 48.

The depolarization determination unit 170 determines the state of the ultrasound transducer unit 46, specifically, the degree of progress of depolarization of the ultrasound transducer 48. In the case of determining the degree of progress of depolarization, the depolarization determination unit 170 calculates a depolarization determination value that is an index value. In addition, the depolarization determination unit 170 determines whether or not the calculated depolarization determination value satisfies numerical conditions. The numerical conditions are set for the depolarization determination value, and are recorded on the ultrasound processor apparatus 14 side. As shown in FIG. 4, the depolarization determination unit 170 is connected to the CPU 152. In a case where it is determined that the depolarization determination value satisfies the numerical conditions, the depolarization determination unit 170 transmits the determination result to the CPU 152. The series of processing by the depolarization determination unit 170 (calculation of the depolarization determination value and condition determination regarding the depolarization determination value) will be described in detail in the "Operation example of the ultrasound diagnostic apparatus" later.

As shown in FIG. 4, the DSC 154 is connected to the ASIC 148, and converts (raster conversion) the signal of the image generated by the B mode image generation unit 162, the PW mode image generation unit 164, or the CF mode image generation unit 166 into an image signal according to a normal television signal scanning method, performs various kinds of required image processing, such as gradation processing, on the image signal, and then outputs an obtained signal to the monitor 20.

The memory controller 151 stores the image signal generated by the B mode image generation unit 162, the PW mode image generation unit 164, or the CF mode image generation unit 166 in the cine memory 150. The cine memory 150 has a capacity for storing an image signal for one frame or several frames. The image signal generated by the ASIC 148 is output to the DSC 154, and is also stored in the cine memory 150 by the memory controller 151. In the freeze mode, the memory controller 151 reads the image signal stored in the cine memory 150 and outputs the read image signal to the DSC 154. As a result, in the freeze mode, an ultrasound image (still image) based on the image signal read from the cine memory 150 is displayed on the monitor 20.

The polarization processing unit 155 performs polarization processing, and is formed by a polarization circuit 156 and a circuit switch 158 as shown in FIG. 4. The polarization circuit 156 forms a polarization voltage supply unit, and supplies a polarization voltage to the ultrasound transducer 48. The polarization voltage is a voltage for polarizing the ultrasound transducer 48 (strictly speaking, a piezoelectric element provided in the ultrasound transducer 48). By applying the polarization voltage to the electrodes of the ultrasound transducer 48, the ultrasound transducer 48 is polarized (that is, the alignment direction of the polarizer is one direction).

The polarization circuit 156 is electrically connected to all of the plurality of ultrasound transducers 48 through the universal cord 26 and the coaxial cable 56. In the present embodiment, the polarization circuit 156 is provided separately from the transmission circuit 144 as shown in FIG. 4, and supplies the polarization voltage to the ultrasound transducer 48 in a period during which the operation mode is the second mode. In addition, the polarization voltage is supplied from the polarization circuit 156 to the ultrasound transducer 48 through the multiplexer 140. In the present embodiment, the polarization voltage is supplied to m polarization target transducers simultaneously selected by the multiplexer 140.

The polarization voltage may be a DC voltage or an AC voltage. In a case where the polarization voltage is an AC voltage, the waveform may be a continuous waveform or a pulse waveform. In a case where the waveform of the polarization voltage is a pulse waveform, the waveform may be a unipolar pulse or a bipolar pulse.

As shown in FIG. 4, the circuit switch 158 is connected to both the transmission circuit 144 and the polarization circuit 156 at a position before the multiplexer 140, and is a switch for switching to a circuit to be connected to the multiplexer 140 between the transmission circuit 144 and the polarization circuit 156. The circuit switch 158 normally connects the transmission circuit 144 to the multiplexer 140. In this state, a driving voltage for ultrasound wave transmission is supplied to the driving target transducer. On the other hand, at the time of execution of polarization processing, the circuit switch 158 switches a circuit to be connected to the multiplexer 140 from the transmission circuit 144 to the polarization circuit 156. In this state, a polarization voltage is supplied to the ultrasound transducer 48 to be polarized.

The CPU 152 functions as a controller that controls each unit of the ultrasound processor apparatus 14. As shown in FIG. 4, the CPU 152 is connected to the reception circuit 142, the transmission circuit 144, the A/D converter 146, the ASIC 148, the polarization circuit 156, and the circuit switch 158 to control these devices. Specifically, the CPU 152 is connected to the console 100 as shown in FIG. 4, and controls each unit of the ultrasound processor apparatus 14 according to examination information and control parameters input through the console 100 at the time of ultrasound diagnosis. As a result, an ultrasound image corresponding to the ultrasound image generation mode designated by the operator is acquired. In particular, in the live mode, an ultrasound image is acquired as needed at a fixed frame rate.

The CPU 152 automatically recognizes the ultrasound endoscope 12 based on a method, such as Plug and Play (PnP), in a case where the ultrasound endoscope 12 is connected to the ultrasound processor apparatus 14 through the ultrasound connector 32*a*. Thereafter, the CPU 152 accesses the endoscope side memory 58 of the ultrasound endoscope 12 to read the cumulative value of the driving time stored in the endoscope side memory 58. In addition, the CPU 152 accesses the endoscope side memory 58 at the end of the ultrasound diagnosis, and updates the cumulative value of the driving time stored in the endoscope side memory 58 to a value obtained by adding the time required for the ultrasound diagnosis performed immediately before to the cumulative value of the driving time stored in the endoscope side memory 58.

In the present embodiment, the driving time is stored on the ultrasound endoscope 12 side. However, the invention is not limited thereto, and the driving time may be stored on the ultrasound processor apparatus 14 side for each ultrasound endoscope 12.

In addition, in a case where predetermined conditions are satisfied in a period during which the operation mode is the second mode, the CPU 152 controls the polarization processing unit 155 (specifically, the polarization circuit 156 and the circuit switch 158) so that the polarization processing unit 155 performs polarization processing. In the polarization processing, the polarization circuit 156 supplies a polarization voltage to the ultrasound transducer 48 to be polarized. The magnitude (potential) and the supply time of the polarization voltage supplied to the ultrasound transducer 48 in the polarization processing are set to appropriate values by the CPU 152 according to the specification of the ultrasound transducer 48 (specifically, the thickness, material, and the like of the piezoelectric element). Thereafter, the CPU 152 controls the polarization processing unit 155 based on the set values described above. The magnitude and the supply time of the polarization voltage are not limited to being automatically set by the CPU 152, and may be set to any values input through the console 100 by the operator.

<<Operation Example of Ultrasound Diagnostic Apparatus>>

Figure 5:
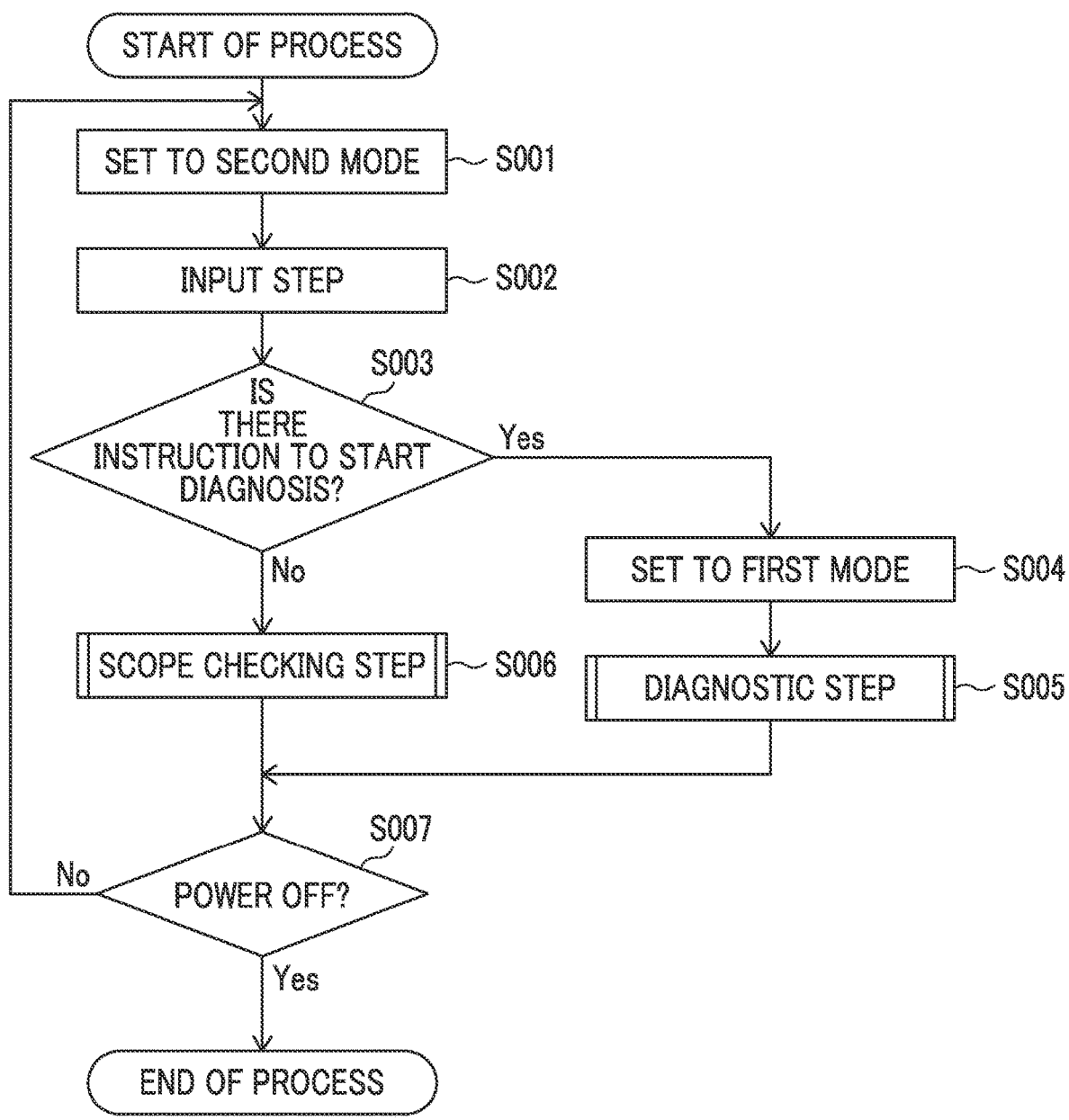
FIG. 5 is a diagram showing the flow of a diagnostic process using the ultrasound diagnostic apparatus.
Figure 6:
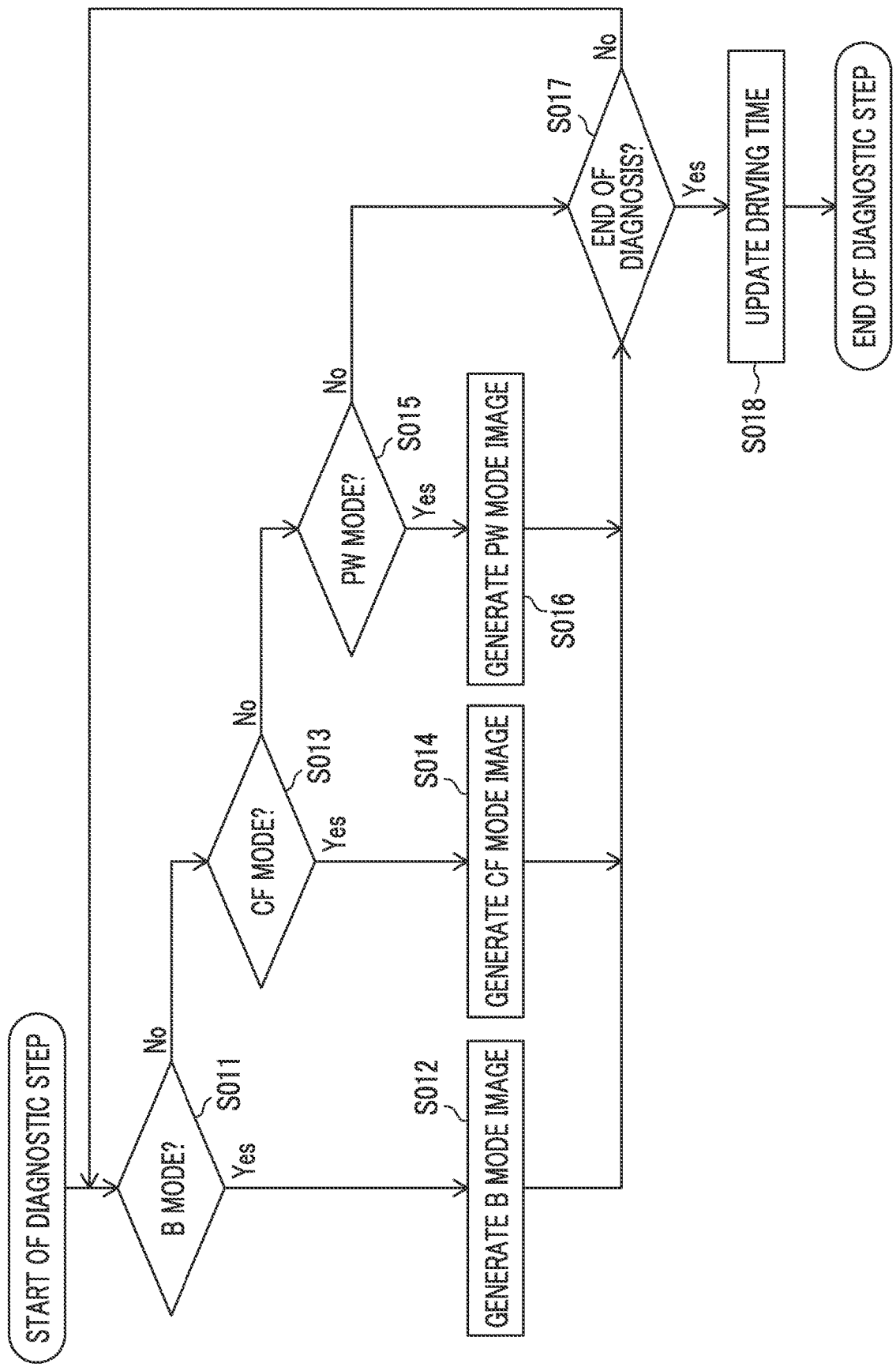
FIG. 6 is a diagram showing the procedure of a diagnostic step in the diagnostic process.
Figure 7:
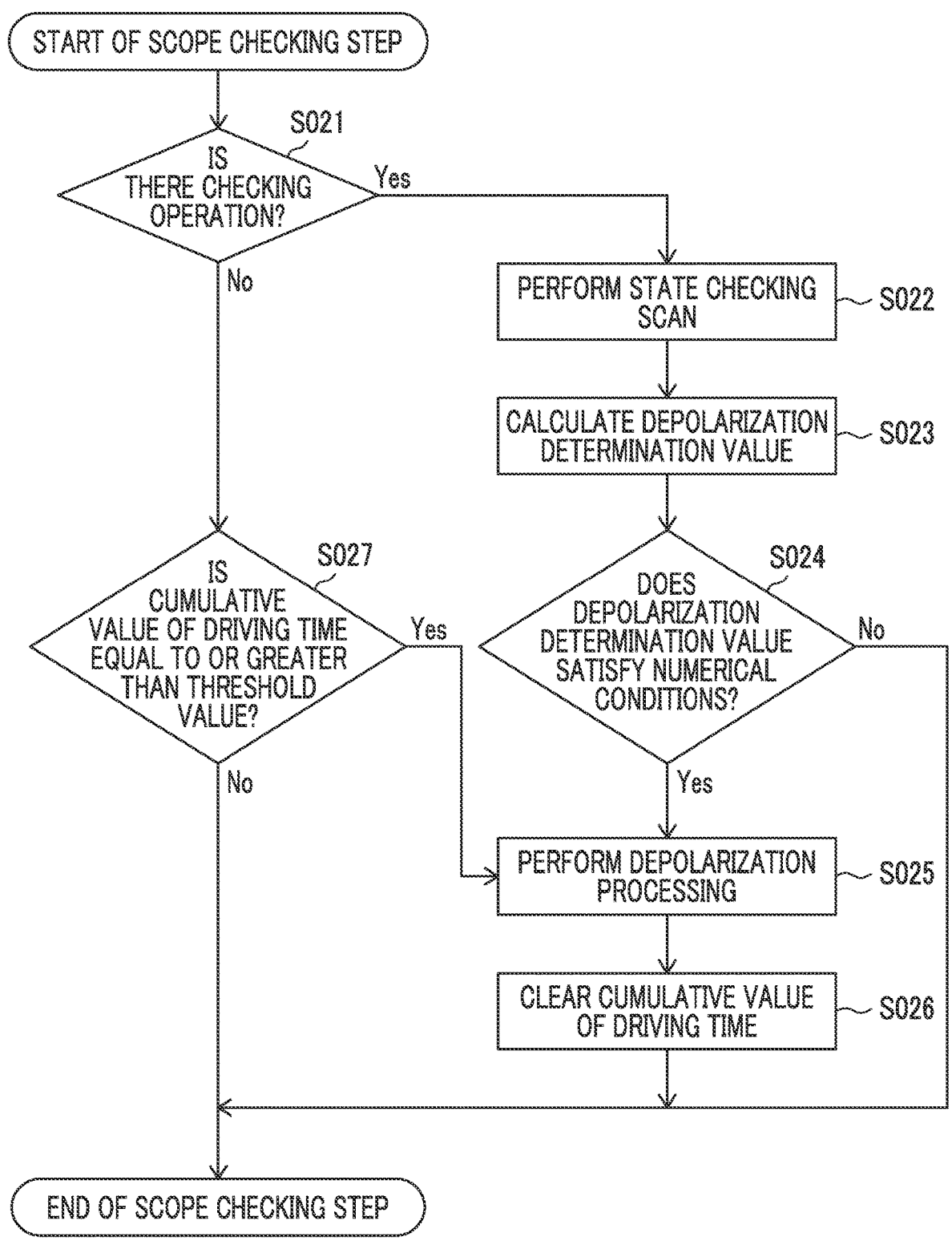
FIG. 7 is a diagram showing the procedure of a scope checking step in the diagnostic process.

Next, as an operation example of the ultrasound diagnostic apparatus 10, a flow of a series of processes relevant to ultrasound diagnosis (hereinafter, also referred to as diagnostic process) will be described with reference to FIGS. 5 to 7. FIG. 5 is a diagram showing the flow of the diagnostic process using the ultrasound diagnostic apparatus 10. FIG. 6 is a diagram showing the procedure of a diagnostic step in the diagnostic process. FIG. 7 is a diagram showing the procedure of a scope checking step in the diagnostic process.

In a case where each unit of the ultrasound diagnostic apparatus 10 is powered on in a state in which the ultrasound endoscope 12 is connected to the ultrasound processor apparatus 14, the endoscope processor apparatus 16, and the light source device 18, the diagnostic process starts with the power-ON as a trigger. In a case where the diagnostic process starts, as shown in FIG. 5, the operation mode is set to the second mode first (S001), and an input step is performed (S002). In the input step, the operator inputs examination information, control parameters, and the like through the console 100.

In a case where there is an instruction to start diagnosis after the end of the input step (Yes in S003), the operation mode is set to the first mode (S004). Thereafter, the operator inserts the insertion part 22 of the ultrasound endoscope 12 into the body cavity of the patient, and the CPU 152 controls each unit of the ultrasound processor apparatus 14 in the state to perform a diagnostic step (S005). The diagnostic step proceeds along the flow shown in FIG. 6. Specifically, in a case where the designated ultrasound image generation mode is a B mode (Yes in S011), the CPU 152 controls each unit of the ultrasound processor apparatus 14 to generate a B mode image (S012). In a case where the designated ultrasound image generation mode is a CF mode (Yes in S013), the CPU 152 controls each unit of the ultrasound processor apparatus 14 to generate a CF mode image (S014). In a case where the designated ultrasound image generation mode is a PW mode (Yes in S015), the CPU 152 controls each unit of the ultrasound processor apparatus 14 to generate a PW mode image (S016).

The generation of an ultrasound image in each mode is repeatedly performed until the diagnosis end conditions are satisfied (S017). As the diagnosis end conditions, for example, the operator gives an instruction to end the diagnosis through the console 100.

In a case where the diagnosis end conditions are satisfied (Yes in S017), as shown in FIG. 6, the CPU 152 accesses the endoscope side memory 58 and updates the cumulative value of the driving time stored in the endoscope side memory 58 by adding the time required for the ultrasound diagnosis performed until then to the cumulative value of the driving time stored in the endoscope side memory 58

(S018). The diagnostic step ends at a point in time at which the series of steps (specifically, steps S011 to S018) in the diagnostic step end. Thereafter, the diagnostic process ends at a point in time at which each unit of the ultrasound diagnostic apparatus 10 is powered off (Yes in S007).

Returning to the explanation of step S003 of the diagnostic process, in a case where there is no instruction to start diagnosis after the end of the input step (No in S003), a scope checking step is performed (S006). The scope checking step proceeds along the flow shown in FIG. 7. Specifically, in the scope checking step, in a case where the checking operation unit 102 of the console 100 is operated by the operator (Yes in S021), the console 100 detects the operation (hereinafter, referred to as a checking operation) and transmits the detection result to the CPU 152 of the ultrasound processor apparatus 14.

In a case where the detection result of the checking operation is received, as shown in FIG. 7, the CPU 152 controls the transmission circuit 144 to perform a state checking scan (S022). The state checking scan is to control the transmission circuit 144 so that the driving voltage is supplied to each of the N ultrasound transducers 48 with all of the N ultrasound transducers 48 as driving target transducers. More specifically, in the state checking scan, a driving voltage is supplied to the ultrasound transducer 48 as a driving target transducer at one end of the N ultrasound transducers 48, and the driving target transducer is shifted one by one and the supply of a driving voltage is repeated up to the ultrasound transducer 48 at the other end. In this manner, the N ultrasound transducers 48 are sequentially driven one by one to transmit and receive ultrasound waves.

In the present embodiment, the state checking scan is performed at a time at which the ultrasound endoscope 12 including the ultrasound transducer unit 46 is located outside the body cavity of the patient. That is, the state checking scan is performed in a state in which the ultrasound transducer unit 46 is exposed in a room (hereinafter, referred to as a diagnostic room) where the ultrasound diagnostic apparatus 10 is disposed. More specifically, the state checking scan is performed in a state in which the ultrasound transducer unit 46 faces a suitable place (for example, a place without people) in the diagnostic room. In this case, each ultrasound transducer 48 that is a driving target transducer receives the ultrasound wave reflected by the acoustic matching layer 76 as a reflected wave (echo) of the ultrasound wave.

Immediately after the execution of the state checking scan, as shown in FIG. 7, the depolarization determination unit 170 calculates a depolarization determination value (S023). In step S023, the depolarization determination unit 170 calculates, for each ultrasound transducer 48, reception sensitivity in a case where the ultrasound transducer unit 46 receives ultrasound waves (strictly speaking, ultrasound waves reflected by the acoustic matching layer 76) during the state checking scan. Specifically, the depolarization determination unit 170 is connected to the A/D converter 146 as shown in FIG. 4. The reception signal output from each ultrasound transducer 48 during the state checking scan is digitally converted by the A/D converter 146, and is transmitted from each ultrasound transducer 48 to the depolarization determination unit 170. The depolarization determination unit 170 calculates the reception sensitivity for each ultrasound transducer 48 based on the digitally converted reception signal (reception data). The reception sensitivity for each ultrasound transducer 48 calculated as described above corresponds to reception sensitivity at a time at which the ultrasound transducer unit 46 receives ultrasound waves with all of the N ultrasound transducers 48 as driving target transducers.

Figure 8A:
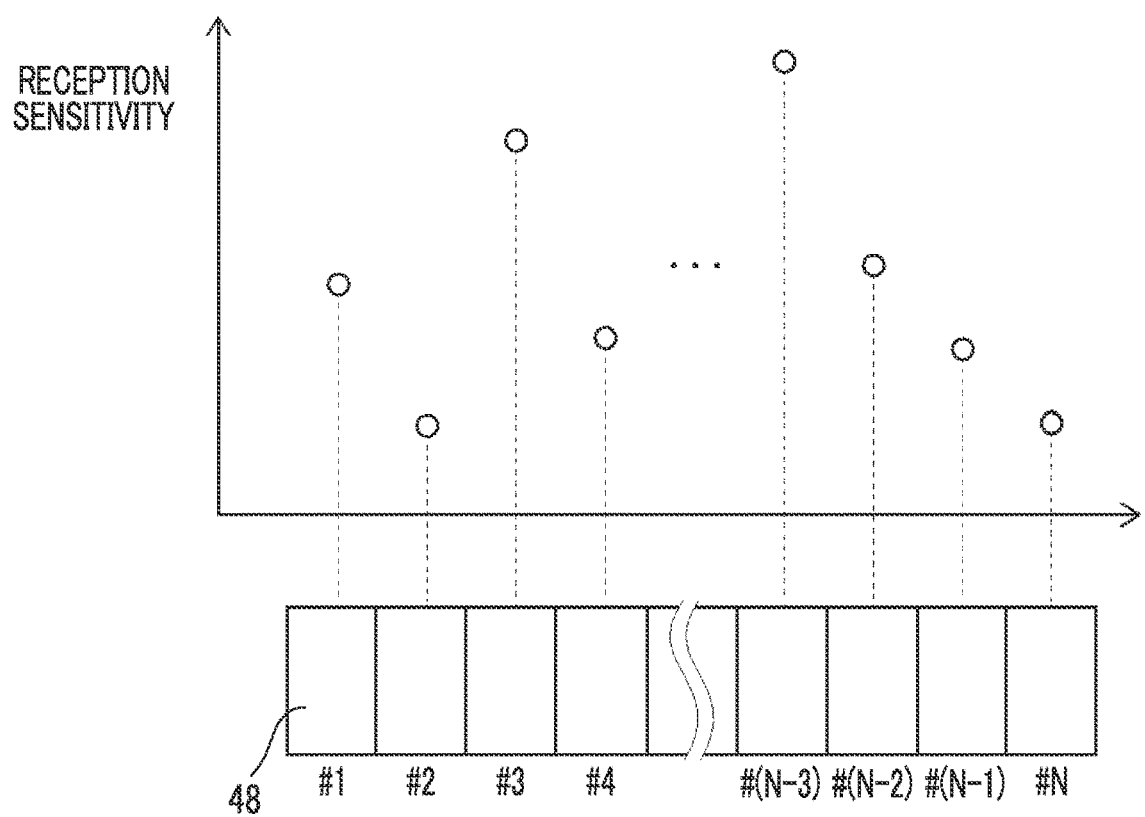
FIG. 8A is a diagram showing the reception sensitivity of each ultrasound transducer (first example).

Here, the reception sensitivity of each ultrasound transducer 48 reflects the degree of progress of depolarization of the ultrasound transducer 48. Specifically, the depolarization proceeds as the driving time of the ultrasound transducer 48 increases, and the reception sensitivity decreases as the depolarization progresses. In addition, the reception sensitivity of each ultrasound transducer 48 varies as shown in FIG. 8A as the number of executions of ultrasound diagnosis increases. This reflects that the number of driving target transducers and the driving frequency of each ultrasound transducer 48 change according to the type (mode) of an ultrasound image formed in ultrasound diagnosis. FIG. 8A is a diagram showing the reception sensitivity of each ultrasound transducer 48. #1, #2, . . . , and #N in the diagram indicate numbers assigned for convenience to identify each ultrasound transducer 48, and a white circle plot directly above the ultrasound transducer 48 of each number indicates the reception sensitivity of the ultrasound transducer 48.

Then, the depolarization determination unit 170 calculates a depolarization determination value from the reception sensitivity calculated for each ultrasound transducer 48. The depolarization determination unit 170 calculates one of the following (d1) to (d7) as the depolarization determination value.

(d1) Variance of reception sensitivity of each ultrasound transducer 48 (hereinafter, referred to as a variance)
(d2) Average value of reception sensitivity of each ultrasound transducer 48 (hereinafter, referred to as an average value)
(d3) Variance and average value
(d4) Minimum value of reception sensitivity of each ultrasound transducer 48 (hereinafter, referred to as a minimum value)
(d5) Variance and minimum value
(d6) Average value and minimum value
(d7) Variance, average value, and minimum value The variance is a statistical dispersion, is calculated with the N ultrasound transducers 48 as a population, and is calculated from the reception sensitivity of each of the N ultrasound transducers 48. The average value is an arithmetic average value calculated from the reception sensitivity of each of the N ultrasound transducers 48. The minimum value of the reception sensitivity of each ultrasound transducer 48 is a minimum value (value closest to 0) among the reception sensitivities of the N ultrasound transducers 48. Hereinafter, a case where the depolarization determination unit 170 calculates the depolarization determination value (that is, the variance and the average value) shown in the above (d3) will be described as an example. However, it is needless to say that the following content can also be applied to a case of calculating other depolarization determination values (specifically, depolarization determination values shown in (d1), (d2), and any one of (d4) to (d7)).

After calculating the depolarization determination value, as shown in FIG. 7, the depolarization determination unit 170 determines whether or not the depolarization determination value satisfies the numerical conditions (S024). The numerical conditions are set for the depolarization determination value, and are recorded on the ultrasound processor apparatus 14 side. In a case where a plurality of types of values are calculated as depolarization determination values, the above-described numerical conditions are set for each depolarization determination value. For example, in a case where a variance is calculated as a depolarization determination value, an upper limit is set as the numerical conditions, and the depolarization determination unit 170 determines whether or not the variance exceeds the upper limit. In a case where at least one of an average value or a minimum value is calculated as a depolarization determination value, a lower limit is set as the numerical conditions, and the depolarization determination unit 170 determines whether or not the calculated value (that is, at least one of the average value or the minimum value) is less than the lower limit. The numerical conditions may be different for each ultrasound endoscope 12, or may be common among the ultrasound endoscopes 12. In addition, the operator may be able to newly set or change the numerical conditions through the console 100.

Then, in a case where it is determined that the depolarization determination value satisfies the numerical conditions (Yes in S024), the depolarization determination unit 170 transmits the determination result to the CPU 152. In a case where a plurality of types of values (for example, a variance and an average value) are calculated as depolarization determination values, it is determined that any one determination value satisfies the numerical conditions, the depolarization determination unit 170 transmits the determination result to the CPU 152.

The above-described series of steps, that is, the checking scan execution step S022, the depolarization determination value calculation step S023, and the conditions determination step S024 regarding the depolarization determination value are performed with a checking operation, which is performed by the operator through the checking operation unit 102 in a period during which the operation mode is the second mode, as a trigger. Then, the degree of progress of depolarization is estimated by the execution of steps S022, S023, and S024, and the depolarization progresses in a case where the depolarization determination value satisfies the above-described numerical conditions. Here, the degree of progress of the depolarization is usually evaluated based on the reception sensitivity of the ultrasound transducer 48, but the reception sensitivity of each ultrasound transducer 48 in the ultrasound transducer unit 46 varies between the ultrasound transducers 48. In a case where the ultrasound transducer unit 46 is a convex type probe, the variation is noticeable. For this reason, since it is not sufficient to determine the degree of progress of depolarization based only on the reception sensitivity of one of the ultrasound transducers 48, it is necessary to determine the degree of progress of the depolarization based on the above-described variation. Therefore, in the present embodiment, as described above, the reception sensitivity of each of the N ultrasound transducers 48 is calculated, and the degree of progress of depolarization is determined based on the depolarization determination value calculated from the reception sensitivity of each ultrasound transducer 48.

Returning to the explanation of the scope checking step, as shown in FIG. 7, in a case where the determination result indicating that the depolarization determination value satisfies the numerical conditions is received, the CPU 152 controls the polarization processing unit 155 (that is, the polarization circuit 156 and the circuit switch 158) so that the polarization processing unit 155 performs polarization processing (S025). That is, in a case where the depolarization determination unit 170 determines that the depolarization determination value satisfies the numerical conditions, the polarization circuit 156 that is a polarization voltage supply unit supplies a polarization voltage to the ultrasound transducer 48 to be polarized through the multiplexer 140. In the present embodiment, the polarization processing is performed on all of the N ultrasound transducers 48. Specifically, half (that is, m ultrasound transducers 48) of the N ultrasound transducers 48 are polarized in the first half of the polarization processing, and the other half of the ultrasound transducers 48 are polarized in the second half.

Figure 8B:
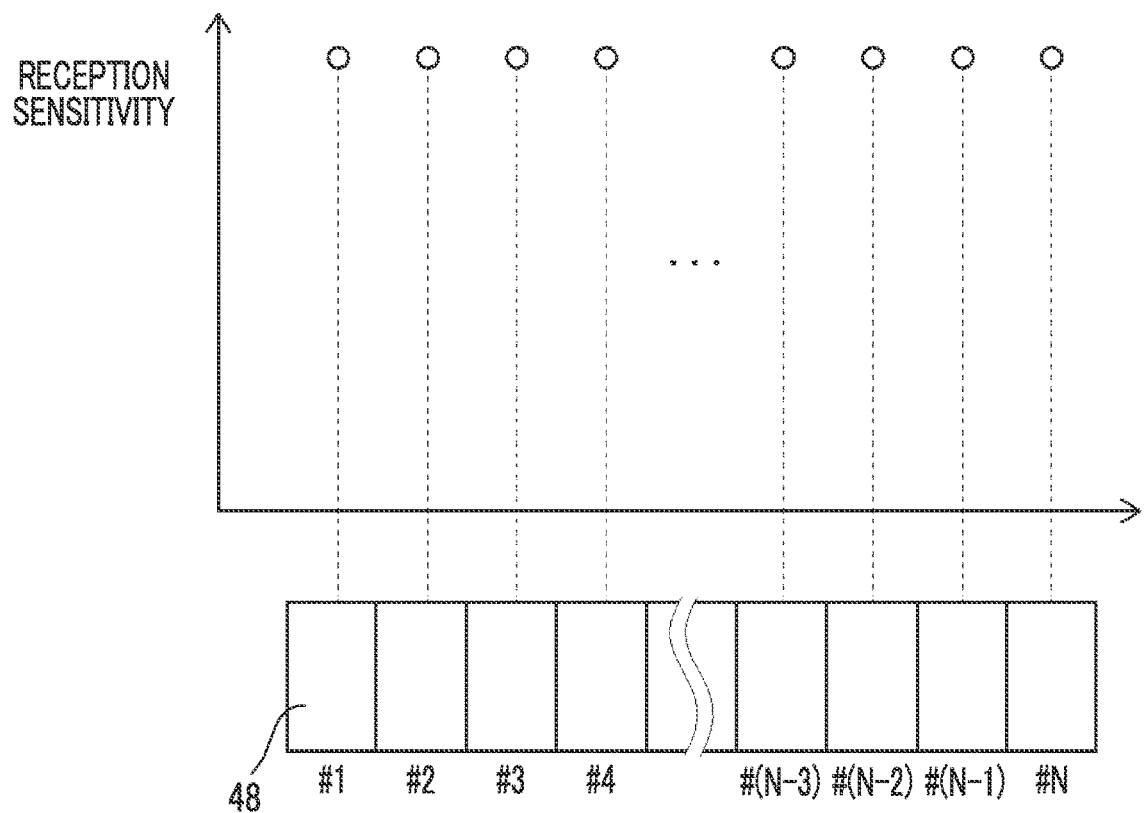
FIG. 8B is a diagram showing the reception sensitivity of each ultrasound transducer (second example).

By performing the polarization processing, as shown in FIG. 8B, each ultrasound transducer 48 is polarized (repolarized). Accordingly, the reception sensitivity of each ultrasound transducer 48 is restored, and the reception sensitivities of the ultrasound transducers 48 become approximately the same. FIG. 8B is a diagram showing the reception sensitivity of each ultrasound transducer 48 immediately after the polarization processing is performed, and is a diagram corresponding to FIG. 8A.

In a case where a variance and an average value are calculated as depolarization determination value, the polarization processing is performed in a case where at least one of the values satisfies the numerical conditions. Therefore, for example, in a case where the reception sensitivities of the N ultrasound transducers 48 are entirely reduced, it is possible to recover the reception sensitivity of each ultrasound transducer 48 by performing polarization processing in a case where the average value is lower than the lower limit even in a case where the variance does not exceed the upper limit.

After the polarization circuit 156 supplies a polarization voltage to each of the N ultrasound transducers 48 in the polarization processing, as shown in FIG. 7, the CPU 152 accesses the endoscope side memory 58 to clear the cumulative value of the driving time stored in the endoscope side memory 58 (S026). As a result, the cumulative value of the driving time stored in the endoscope side memory 58 is set to the initial value (that is, zero (0)). Then, the scope checking step ends at a point in time at which the cumulative value of the driving time is cleared. Also in a case where the depolarization determination unit 170 determines that the depolarization determination value does not satisfy the numerical conditions in step S024 (No in S024), the scope checking step ends.

On the other hand, in a case where the checking operation is not performed in step S021 (No in S021), the CPU 152 reads the cumulative value of the driving time from the endoscope side memory 58 and determines whether or not the cumulative value is equal to or greater than the threshold value (S027). The threshold value is set based on an input operation performed by the operator through the threshold value input unit 104 of the console 100, and is stored, for example, on the ultrasound processor apparatus 14 side. The threshold value may be different for each ultrasound endoscope 12, or may be a value common to the ultrasound endoscopes 12.

Then, in a case where it is determined that the above-described cumulative value is equal to or greater than the threshold value, the CPU 152 controls the polarization processing unit 155 so that the polarization processing unit 155 performs polarization processing as shown in FIG. 7 (S025). That is, in a case where the cumulative value of the driving time stored in the endoscope side memory 58 is equal to or greater than the threshold value, the polarization circuit 156 supplies a polarization voltage to the ultrasound transducer 48 to be polarized through the multiplexer 140. Also in this case, the polarization processing is performed on all of the N ultrasound transducers 48, and m ultrasound transducers 48 are polarized in each of the first half and the second half of the polarization processing.

After the polarization processing is performed, as shown in FIG. 7, the CPU 152 clears the cumulative value of the driving time stored in the endoscope side memory 58 (S026), and ends the scope checking step at a point in time at which step S026 is completed. Also in a case where the CPU 152 determines that the cumulative value of the driving time is less than the threshold value in step S027 (No in S027), the scope checking step ends.

<<Effectiveness of Ultrasound Diagnostic Apparatus of the Invention>>

The characteristic of the ultrasound diagnostic apparatus of the invention is that a depolarization determination value as an index value regarding the state of the ultrasound transducer unit 46 is calculated with the operator's operation on the checking operation unit 102 as a trigger, the necessity of polarization processing is determined from the depolarization determination value, and the polarization processing is performed in a case where it is determined that the polarization processing is required. That is, in the ultrasound diagnostic apparatus of the invention, since the necessity of polarization processing is determined at a time at which the operator (user) operates the checking operation unit 102, it is possible to determine the necessity of polarization processing at the timing desired by the operator. That is, in the ultrasound diagnostic apparatus of the invention, since the execution timing of the polarization processing is not limited to a predetermined timing unlike in the ultrasound diagnostic apparatus described in JP2013-005137A, the degree of freedom in the execution timing of the polarization processing is increased.

In addition, in the case of determining the necessity of polarization processing based only on the cumulative value of the driving time of the ultrasound transducer 48, even though the operator notices a decrease in the reception sensitivity, it is determined that the polarization processing is not yet required in a case where the cumulative value of the driving time at that point in time is less than the threshold value. In contrast, in the invention, in a case where the operator operates the checking operation unit 102 at a time at which the operator notices a decrease in the reception sensitivity, the necessity of the polarization processing is determined at that point in time. As a result, it is possible to accurately perform the polarization processing at the time at which the polarization processing is to be performed (for example, in a case where the cumulative value of driving time is less than the threshold value but the reception sensitivity is noticeably reduced).

In addition, the ultrasound diagnostic apparatus of the invention does not require the reference transducer that is provided in the ultrasound transducer unit 46 in order to determine the necessity of polarization processing (strictly speaking, the degree of progress of depolarization) in the ultrasound diagnostic apparatus described in JP2013-161955A. Therefore, in the ultrasound diagnostic apparatus of the invention, the ultrasound transducer unit 46 is made smaller than that in the apparatus described in JP2013-161955A. As a result, the operability (ease of insertion of the ultrasound endoscope 12 into the body cavity of the patient) is improved.

In the ultrasound diagnostic apparatus of the invention, in the case of determining the necessity of the polarization processing, the reception sensitivities of all of the plurality of ultrasound transducers 48 are calculated separately for each ultrasound transducer 48, the depolarization determination value is calculated from the reception sensitivity of each ultrasound transducer 48, and it is determined whether or not the depolarization determination value satisfies the numerical conditions. That is, in the ultrasound diagnostic apparatus of the invention, the depolarization determination value can be calculated from the reception sensitivities of all of the plurality of ultrasound transducers 48 based on the fact that the reception sensitivity (in other words, the degree of progress of depolarization) varies between the ultrasound transducers 48, and the necessity of the polarization processing can be determined based on the depolarization determination value. As a result, a more appropriate determination result can be obtained as compared with the ultrasound diagnostic apparatus described in JP2012-139460A in which a variation in the degree of progress of depolarization is not considered in the determination regarding the necessity of the polarization processing.

Second Embodiment

In the embodiment described above, it is assumed that the checking operation unit 102 for checking the state of the ultrasound transducer unit 46 is provided in an apparatus other than the ultrasound endoscope 12, specifically, in the console 100. However, the invention is not limited thereto, and an embodiment in which the checking operation unit is provided in the ultrasound endoscope 12 (hereinafter, also referred to as a second embodiment) can also be considered.

Figure 9:
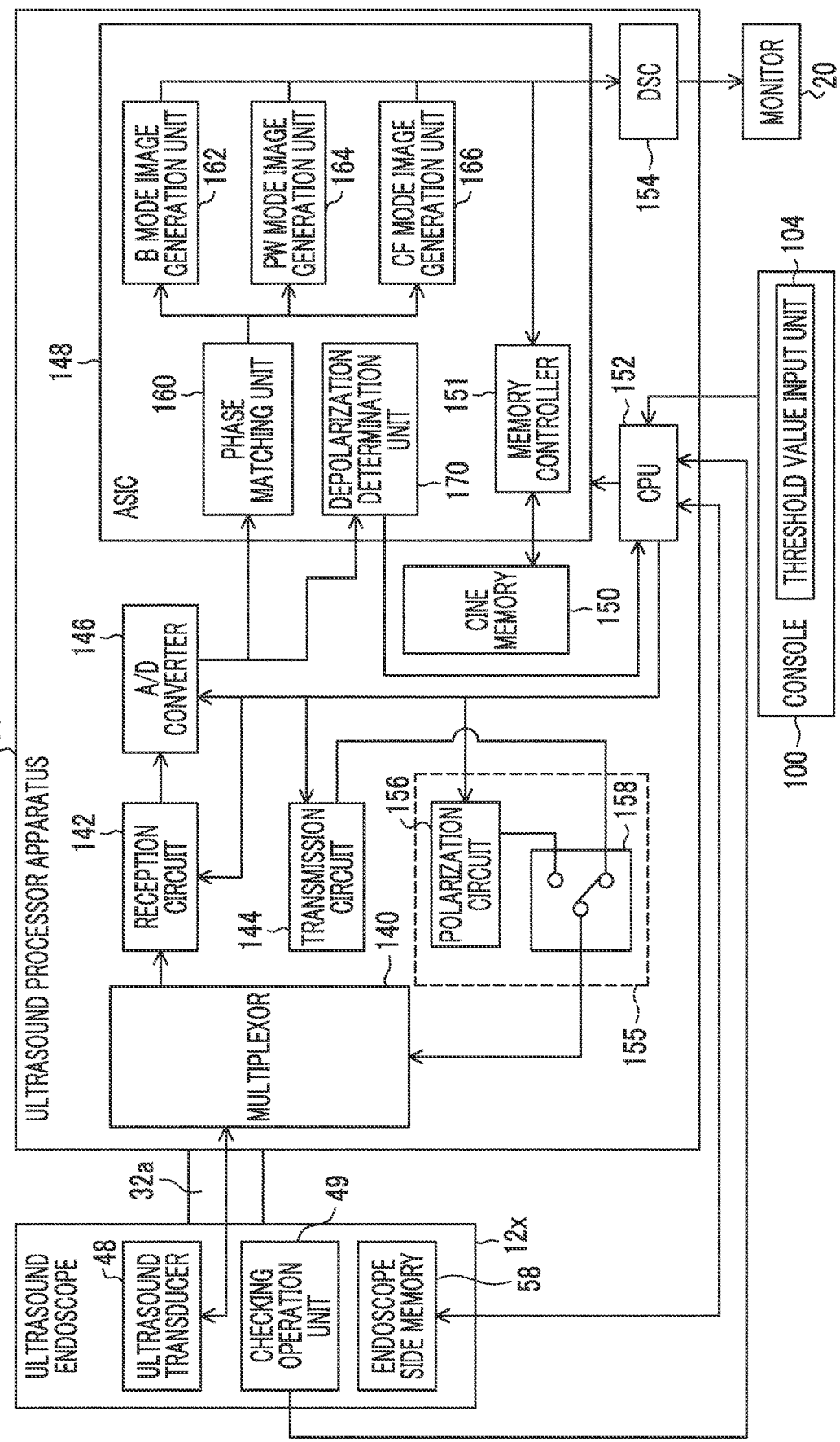
FIG. 9 is a block diagram showing the configurations of an ultrasound endoscope and an ultrasound processor apparatus according to a second embodiment.

Hereinafter, an ultrasound diagnostic apparatus according to the second embodiment will be described with reference to FIG. 9. FIG. 9 is a block diagram showing the configurations of an ultrasound endoscope 12x and an ultrasound processor apparatus 14 that are provided in the ultrasound diagnostic apparatus according to the second embodiment. Hereinafter, the second embodiment will be described focusing on the differences from the above-described embodiment. In the second embodiment, in FIG. 9, elements in common with the above-described embodiment are denoted by the same reference numerals as in the above-described embodiment, and the description thereof will be omitted.

In the second embodiment, the checking operation unit 102 is not provided in the console 100, while a checking operation unit 49 is provided in the ultrasound endoscope 12. That is, in the second embodiment, in the case of checking the state of the ultrasound transducer unit 46 (in other words, in the case of determining the necessity of polarization processing), the operator operates the checking operation unit 49 of the ultrasound endoscope 12. The checking operation unit 49 of the ultrasound endoscope 12 may be formed by, for example, a push button, a slide switch, a dial switch, or a handle such as a lever provided in the operation unit 24.

The checking operation unit 49 is connected to the CPU 152, and outputs a signal to the CPU 152 in a case where the checking operation unit 49 is operated while the operation mode is the second mode. In a case where the output signal from the checking operation unit 49 is received, the CPU 152 performs a state checking scan. The subsequent procedures are similar to those in the above-described embodiment. As described above, in the second embodiment, since the checking operation unit 49 is provided in the ultrasound endoscope 12, the operator can perform an operation for checking the state of the ultrasound transducer unit 46 while operating the ultrasound endoscope 12. As a result, it is possible to improve the convenience of the operator. The second embodiment is the same as the above-described embodiment except that the checking operation unit 49 is provided in the ultrasound endoscope 12. Accordingly, the same effect as in the above-described embodiment is obtained.

Third Embodiment

In the above-described embodiment, it is assumed that the state checking scan is performed in a state in which the ultrasound transducer unit 46 is exposed in the diagnostic room, specifically, the state checking scan is performed in a state in which the ultrasound transducer unit 46 faces a suitable place in the diagnostic room. In addition, in the above-described embodiment, in the state checking scan, it is assumed that each ultrasound transducer 48 that is a driving target transducer receives the ultrasound wave reflected by the acoustic matching layer 76 as a reflected wave (echo) of the ultrasound wave. However, the invention is not limited thereto, and other methods can be considered as methods for performing the state checking scan.

Figure 10:
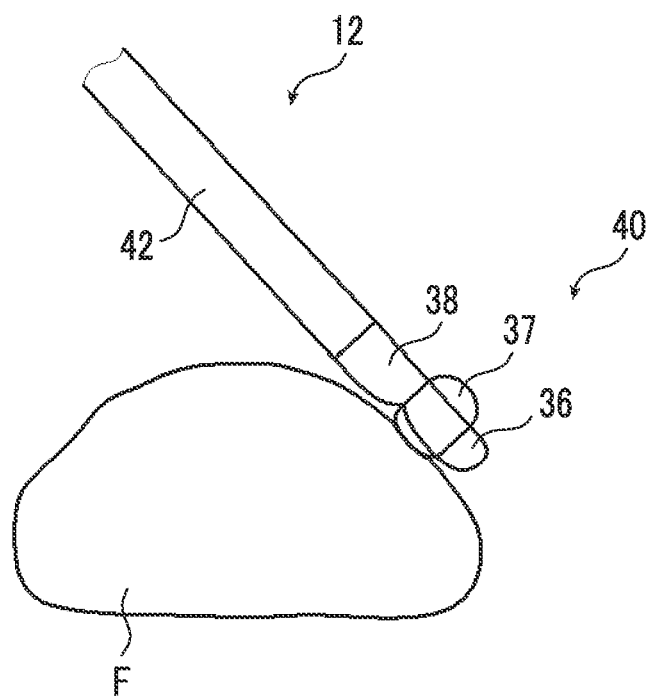
FIG. 10 is an explanatory diagram of a state checking scan in a third embodiment.

Hereinafter, an embodiment (hereinafter, referred to as a third embodiment) for performing a state checking scan using a method different from the methods of the above-described embodiments will be described with reference to FIG. 10. FIG. 10 is an explanatory diagram of the state checking scan in the third embodiment. Hereinafter, the third embodiment will be described focusing on the differences from the above-described embodiments. In the third embodiment, in FIG. 10, elements in common with the above-described embodiments are denoted by the same reference numerals as in the above-described embodiments, and the description thereof will be omitted.

In the third embodiment, the state checking scan is performed in a state in which the ultrasound endoscope 12 is not inserted into the body cavity of the patient, that is, in a state in which the ultrasound endoscope 12 is located outside the body of the patient. More specifically, in the third embodiment, a phantom F (for example, a human model) shown in FIG. 10 is disposed outside the body of the patient. At the time of performing the state checking scan, the operator presses the ultrasound transducer unit 46 (strictly speaking, the exposed surface of the acoustic lens 78) against the phantom F as shown in FIG. 10. Thereafter, in a case where the operator operates the checking operation unit 102 in a state in which the ultrasound transducer unit 46 is in contact with the phantom F, the CPU 152 performs the state checking scan with the operation as a trigger. In the state checking scan, the ultrasound transducer unit 46 transmits and receives ultrasound waves using all of the N ultrasound transducers 48 as driving target transducers. In this case, the ultrasound transducer unit 46 receives an ultrasound wave (echo) reflected by the phantom F. Thereafter, the depolarization determination unit 170 calculates the reception sensitivity of each of the N ultrasound transducers 48 in the state checking scan, and further calculates the depolarization determination value. The subsequent procedures are similar to those in the above-described embodiments.

As described above, in the third embodiment, the state checking scan is performed using the phantom F, and the ultrasound transducer unit 46 receives an ultrasound wave (echo) reflected by the phantom F in the state checking scan. Since the strength of the ultrasound wave reflected by the phantom F is usually larger than the strength of the ultrasound wave reflected by the acoustic matching layer 76, it is possible to calculate the reception sensitivity of each ultrasound transducer 48 more appropriately by performing the state checking scan using the phantom F. The third embodiment is the same as the above-described embodiments except that the state checking scan is performed using the phantom F. Accordingly, the same effect as in the above-described embodiments is obtained.

Fourth Embodiment

In the above-described embodiments, the polarization voltage supply unit is formed by the polarization circuit 156 provided separately from the transmission circuit 144, the invention is not limited thereto. For example, an embodiment in which the transmission circuit 144 is also used as a polarization voltage supply unit (hereinafter, also referred to as a fourth embodiment) can also be considered.

Figure 11:
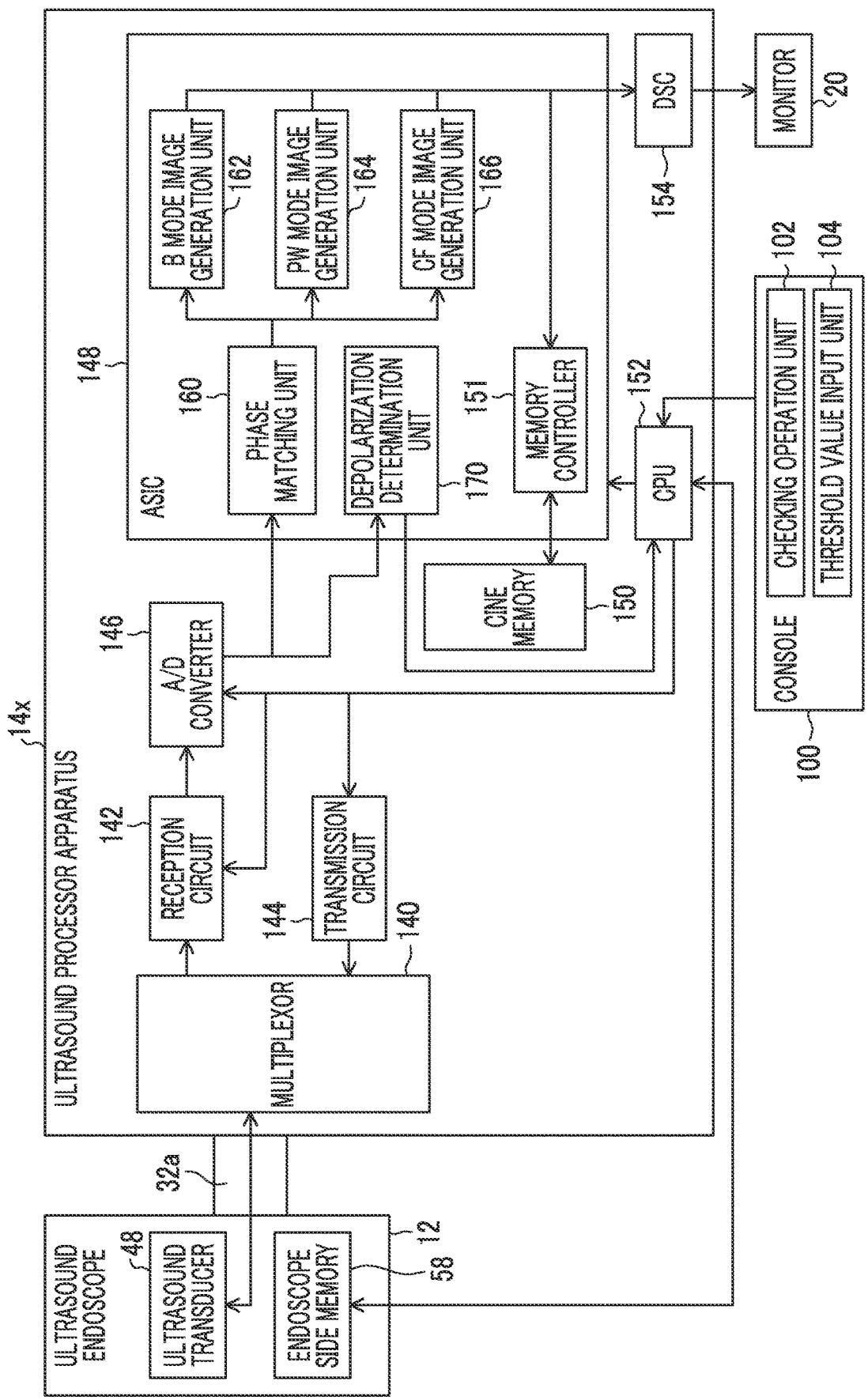
FIG. 11 is a block diagram showing the configuration of an ultrasound processor apparatus according to a fourth embodiment.
Figure 12:
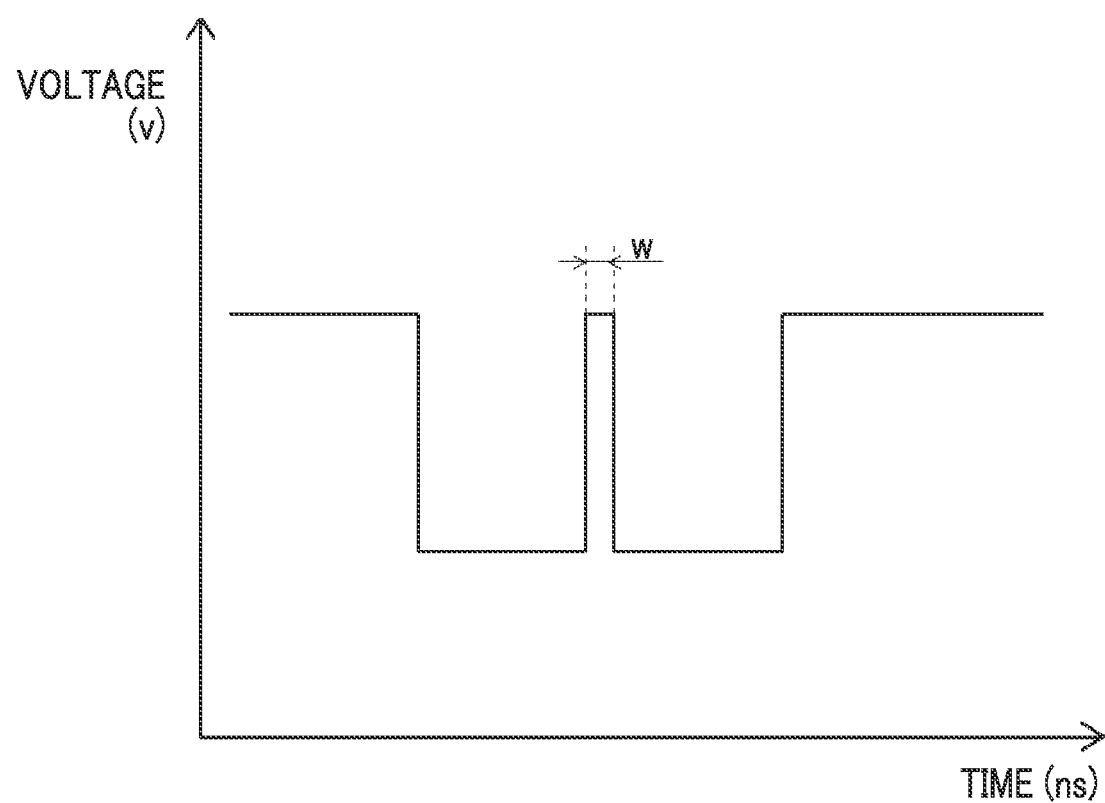
FIG. 12 is a diagram showing the waveform of a polarization voltage supplied in the fourth embodiment.

Hereinafter, an ultrasound diagnostic apparatus according to the fourth embodiment will be described with reference to FIGS. 11 and 12. FIG. 11 is a block diagram showing the configuration of an ultrasound processor apparatus 14x according to the fourth embodiment. FIG. 12 is a diagram showing the waveform of a polarization voltage supplied in the fourth embodiment. Hereinafter, the fourth embodiment will be described focusing on the differences from the above-described embodiments. In the fourth embodiment, in FIG. 11, elements in common with the above-described embodiments are denoted by the same reference numerals as in the above-described embodiments, and the description thereof will be omitted.

The ultrasound processor apparatus 14x of the fourth embodiment does not comprise a device corresponding to the polarization processing unit 155 as shown in FIG. 11. On the other hand, in the fourth embodiment, the transmission circuit 144 forms a polarization voltage supply unit, and supplies a polarization voltage to each of the N ultrasound transducers 48 in a case where the polarization conditions are satisfied in the scope checking step (that is, in a case where it is determined that polarization processing needs to be performed). That is, in the fourth embodiment, the CPU 152 controls the transmission circuit 144 so that the transmission circuit 144 outputs a driving voltage in the diagnostic step and outputs a polarization voltage in the scope checking step.

In the fourth embodiment, the polarization voltage supplied by the transmission circuit 144 is a pulse wave voltage similar to the driving voltage, more specifically, a unipolar pulse voltage. In the fourth embodiment, for the purpose of efficiently performing polarization, as shown in FIG. 12, the CPU 152 controls the transmission circuit 144 so that the polarization voltage, which is a unipolar pulse, is intermittently supplied a plurality of times from the transmission circuit 144. Here, a pulse wave interval (w in FIG. 12) corresponds to a plurality of clock signals input to the transmission circuit 144, specifically, an interval of a degree that a plurality of polarization voltage waveforms intermittently arranged form a DC waveform in a pseudo manner. For the purpose of bringing the waveform of the polarization voltage close to the DC waveform, the interval described above is preferably as short as possible. In particular, it is preferable to set the interval described above to an interval corresponding to the minimum clock.

As described above, in the fourth embodiment, since the transmission circuit 144 forms a polarization voltage supply unit, it is possible to polarize the ultrasound transducer 48 using the existing transmission circuit 144. As a result, since it is not necessary to separately provide the polarization circuit 156, the hardware configuration of the ultrasound processor apparatus 14x is simplified accordingly. In this respect, the fourth embodiment is preferable. On the other hand, providing the transmission circuit 144 and the polarization circuit 156 separately is advantageous in that it is possible to shorten the time of polarization processing. In this respect, the above-described embodiments are preferable.

In addition, the fourth embodiment is different from the above-described embodiments in that the transmission circuit 144 forms a polarization voltage supply unit but is the same as the above-described embodiments other than that. Therefore, the same effect as in the above-described embodiments is obtained.

EXPLANATION OF REFERENCES

- 10: ultrasound diagnostic apparatus
- 12: ultrasound endoscope
- 12x: ultrasound endoscope
- 14: ultrasound processor apparatus
- 14x: ultrasound processor apparatus
- 16: endoscope processor apparatus
- 18: light source device
- 20: monitor
- 21a: water supply tank
- 21b: suction pump
- 21c: air supply pump
- 22: insertion part
- 24: operation unit
- 26: universal cord
- 28a: air and water supply button
- 28b: suction button
- 30: treatment tool insertion port
- 32a: ultrasound connector
- 32b: endoscope connector
- 32c: light source connector
- 36: ultrasound observation portion
- 37: balloon
- 38: endoscope observation portion
- 40: distal end portion
- 42: bending portion
- 43: flexible portion
- 44: treatment tool lead-out port
- 45: treatment tool channel
- 46: ultrasound transducer unit
- 47: water supply port
- 48: ultrasound transducer
- 49: checking operation unit
- 50: ultrasound transducer array
- 54: backing material layer
- 56: coaxial cable
- 58: endoscope side memory
- 60: FPC
- 76: acoustic matching layer
- 78: acoustic lens
- 82: observation window
- 84: objective lens
- 86: solid-state imaging element
- 88: illumination window
- 90: cleaning nozzle
- 92: wiring cable
- 100: console
- 102: checking operation unit
- 104: threshold value input unit
- 140: multiplexer
- 142: reception circuit
- 144: transmission circuit
- 146: A/D converter
- 148: ASIC
- 150: cine memory
- 151: memory controller
- 152: CPU
- 154: DSC
- 155: polarization processing unit
- 156: polarization circuit
- 158: circuit switch
- 160: phase matching unit
- 162: B mode image generation unit
- 164: PW mode image generation unit
- 166: CF mode image generation unit
- 170: depolarization determination unit
- F: phantom

What is claimed is:

1. An ultrasound diagnostic apparatus, comprising:
a probe that comprises a plurality of ultrasound transducers and transmits and receives ultrasound waves by driving target transducers, among the plurality of ultrasound transducers;
a processor configured to supply a driving voltage to the driving target transducers; and
a button or switch configured to be operable by a user to check a state of the probe,
wherein the processor is configured to:
control such that the driving voltage is supplied to a part or all of the plurality of ultrasound transducers as the driving target transducers to generate an ultrasound image when the user instructs an ultrasound diagnosis;
control such that the driving voltage is supplied to each of the plurality of ultrasound transducers with all of the plurality of ultrasound transducers as the driving target transducers when the button or switch is operated;
when the button or switch is operated, calculate, for each ultrasound transducer, a reception sensitivity when the probe receives an ultrasound wave with all of the plurality of ultrasound transducers as the driving target transducers, and determine whether or not a depolarization determination value calculated from the reception sensitivity of each ultrasound transducer satisfies numerical conditions set for the depolarization determination value; and
supply a polarization voltage to each of the plurality of ultrasound transducers when the depolarization determination value is determined to satisfy the numerical conditions, and
wherein the driving voltage for generating the ultrasound image, the drive voltage for calculating the depolarization determination value, and the polarization voltage are supplied at different timings through a multiplexer.

2. The ultrasound diagnostic apparatus according to claim 1,
wherein processor is configured to calculate at least one of a variance of the reception sensitivity of each ultrasound transducer, an average value of the reception sensitivity of each ultrasound transducer, or a minimum value of the reception sensitivity of each ultrasound transducer as the depolarization determination value.

3. The ultrasound diagnostic apparatus according to claim 1, further comprising:
a memory that stores a cumulative value of a driving time of the driving target transducer,
wherein, when the cumulative value stored in the memory is equal to or greater than a threshold value, the processor is configured to supply the polarization voltage to each of the plurality of ultrasound transducers.

4. The ultrasound diagnostic apparatus according to claim 2, further comprising:
a memory that stores a cumulative value of a driving time of the driving target transducer,
wherein, when the cumulative value stored in the memory is equal to or greater than a threshold value, the processor is configured to supply the polarization voltage to each of the plurality of ultrasound transducers.

5. The ultrasound diagnostic apparatus according to claim 3,
wherein the cumulative value stored in the memory is set to an initial value after the processor supplies the polarization voltage to each of the plurality of ultrasound transducers.

6. The ultrasound diagnostic apparatus according to claim 4,
wherein the cumulative value stored in the memory is set to an initial value after the processor supplies the polarization voltage to each of the plurality of ultrasound transducers.

7. The ultrasound diagnostic apparatus according to claim 3,
wherein a console is provided to receive a user's input operation regarding the threshold value.

8. The ultrasound diagnostic apparatus according to claim 4,
wherein a console is provided to receive a user's input operation regarding the threshold value.

9. The ultrasound diagnostic apparatus according to claim 5,
wherein a console is provided to receive a user's input operation regarding the threshold value.

10. The ultrasound diagnostic apparatus according to claim 6,
wherein a console is provided to receive a user's input operation regarding the threshold value.

11. The ultrasound diagnostic apparatus according to claim 3,
wherein the probe and the memory are provided in an ultrasound endoscope.

12. The ultrasound diagnostic apparatus according to claim 4,
wherein the probe and the memory are provided in an ultrasound endoscope.

13. The ultrasound diagnostic apparatus according to claim 5,
wherein the probe and the memory are provided in an ultrasound endoscope.

14. The ultrasound diagnostic apparatus according to claim 11,
wherein the button or switch is provided in the ultrasound endoscope.

15. The ultrasound diagnostic apparatus according to claim 1,
wherein the probe is a convex type probe in which the plurality of ultrasound transducers are disposed in an arc shape.

16. The ultrasound diagnostic apparatus according to claim 1,
wherein an operation mode of the ultrasound diagnostic apparatus includes a first mode and a second mode,
the probe transmits and receives ultrasound waves to and from an inside of a subject while the operation mode is the first mode,
the probe is located outside the subject while the operation mode is the second mode,
the button or switch is operated while the operation mode is the second mode, and
the processor is configured to supply the polarization voltage to each of the plurality of ultrasound transducers while the operation mode is the second mode.

17. The ultrasound diagnostic apparatus according to claim 1,
wherein the probe has an acoustic matching layer disposed outside the plurality of ultrasound transducers, and
when the button or switch is operated, the processor is configured to control such that the probe transmits ultrasound waves with all of the plurality of ultrasound transducers as the driving target transducers and receives ultrasound waves reflected by the acoustic matching layer.

18. The ultrasound diagnostic apparatus according to claim 1,
wherein the button or switch is operated in a state in which the probe is in contact with a phantom disposed outside a subject, and
when the button or switch is operated, the processor is configured to control such that the probe transmits ultrasound waves with all of the plurality of ultrasound transducers as the driving target transducers and receives ultrasound waves reflected by the phantom.

19. An operation method of an ultrasound diagnostic apparatus according to claim 1, comprising:
transmitting and receiving ultrasound waves by driving the driving target transducers, among the plurality of ultrasound transducers;
supplying the driving voltage to the driving target transducers;
controlling such that the driving voltage is supplied to a part or all of the plurality of ultrasound transducers as the driving target transducers to generate an ultrasound image when the ultrasound diagnosis is instructed;
detecting the button or switch being operated to check a state of the probe;
controlling such that the driving voltage is supplied to each of the plurality of ultrasound transducers with all of the plurality of ultrasound transducers as the driving target transducers when the button or switch is operated;
when the button or switch is operated, calculating, for each ultrasound transducer, the reception sensitivity when the probe receives the ultrasound wave with all of the plurality of ultrasound transducers as the driving target transducers, and determining whether or not the depolarization determination value calculated from the reception sensitivity of each ultrasound transducer satisfies the numerical conditions set for the depolarization determination value; and
supplying a polarization voltage to each of the plurality of ultrasound transducers when the processor determines that the depolarization determination value satisfies the numerical conditions,
wherein the driving voltage for generating the ultrasound image, the drive voltage for calculating the depolarization determination value, and the polarization voltage are supplied at different timings through a multiplexer.

* * * * *